(12) United States Patent
Hancock et al.

(10) Patent No.: US 7,282,345 B1
(45) Date of Patent: Oct. 16, 2007

(54) C-ERBB-2 EXTERNAL DOMAIN: GP75

(75) Inventors: Miriam E. C. Hancock, Oakland, CA (US); John J. Monahan, Orinda, CA (US); Beatrice Claudia Langton, Walnut Creek, CA (US)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 08/158,939

(22) Filed: Nov. 29, 1993

Related U.S. Application Data

(60) Continuation of application No. 07/968,059, filed on Oct. 28, 1992, now abandoned, which is a division of application No. 07/826,231, filed on Jan. 22, 1992, now abandoned, which is a continuation of application No. 07/389,920, filed on Aug. 4, 1989, now abandoned.

(51) Int. Cl.
G01N 33/574 (2006.01)
(52) U.S. Cl. .................. 435/7.23; 435/7.5; 435/7.9; 435/7.92; 436/64; 436/813
(58) Field of Classification Search ............... 435/7.23, 435/7.5, 7.9, 7.92, 7.1, 7.2, 7.21; 436/64, 436/813, 501, 503, 518, 536, 538, 540, 541, 436/542, 543, 544, 545, 546, 547, 548
See application file for complete search history.

(56) References Cited

U.S. PATENT DOCUMENTS

| | | | |
|---|---|---|---|
| 4,699,877 A | 10/1987 | Cline et al. ..................... 435/6 |
| 4,753,894 A | 6/1988 | Frankel et al. |
| 4,933,294 A | 6/1990 | Waterfield et al. .......... 436/501 |
| 4,935,341 A | 6/1990 | Bargmann et al. .............. 435/6 |
| 4,968,603 A | 11/1990 | Slamon et al. ................... 435/6 |
| 5,401,638 A | 3/1995 | Carney et al. ............. 435/7.23 |
| 5,677,171 A | 10/1997 | Hudziak et al. ....... 435/240.27 |
| 5,720,954 A | 2/1998 | Hudziak et al. ......... 424/130.1 |
| 5,725,856 A | 3/1998 | Hudziak et al. ......... 424/130.1 |
| 5,770,195 A | 6/1998 | Hudziak et al. ......... 424/130.1 |
| 5,772,997 A | 6/1998 | Hudziak et al. ......... 424/130.1 |
| 6,015,567 A | 1/2000 | Hudziak et al. ......... 424/277.1 |
| 6,836,414 B1 | 12/2004 | Aaronson et al. |

FOREIGN PATENT DOCUMENTS

| | | |
|---|---|---|
| WO | 8707646 | 12/1987 |
| WO | 8901973 | 3/1989 |
| WO | 8906692 | 7/1989 |
| WO | 8910412 | 11/1989 |
| WO | 9105264 | 4/1991 |

OTHER PUBLICATIONS

Carney, WP, et al., *Journal of Tumor Marker Oncology*, vol. 6, No. 2, pp. 53-72, 1991.*
Masuko, T, et al., *Jpn. J. Cncer Res.*, vol. 80, pp. 10-14, Jan. 1989.*
Drebin, JA, et al., *Oncogene*, vol. 2, pp. 273-277, 1988.*
McKenzie, SJ, et al, *Oncogene*, vol. 4, No. 5, pp. 543-548, May 1989.*
Chan and McGee, "Cellular oncogenes in neoplasia," *J. Clin. Pathol.* 40: 1055-1063 (1987).
Cline and Battifora, "Abnormalities of Protooncogenes in Non-Small Cell Lung Cancer," *Cancer*, 60: 2669-2674 (1987).
Schneider et al., "Differential Expression of the c-erbB-2 Gene in Human Cell and Non-Small Cell Lung Cancer," *Cancer Research*, 49: 4968-4971 (Sep. 15, 1989).
Akiyma et al., "Antibodies to a peptide produced by cancer-related C=erbB-2 gene," *Chemical Abstracts, 107:* 570 (Abstract # 172403m) (1987).
Bargmann et al., "The *neu* oncogene encodes an epidermal growth factor receptor-related protein", *Nature, 319:* 226-230 (1986).
Berger et al., "Correlation of c-*erbB*-2 Gene Amplification and Protein Expression in Human Breast Carcinoma With Nodal Status and Nuclear Grading," *Cancer Research*, 48: 1238-1243 (Mar. 1, 1988).
Bernards et al., "Effective tumor immunotherapy directed against an oncogene-encoded product using a vaccinia virus vector", *PNAS* (USA) 84: 6854-6858 (1987).
Brandt-Rauf et al., "Detection of Increased Amounts of the Extracellular Domain of the c-erbB-2 Oncoprotein in Serum During Pulmonary Carcinogenesis in Humans," *Int. J. Cnacer*, 56: 383-386 (1994).
Breuer et al., "Detection of elevated c-*erbB*-2 oncoprotein in the serum and tissue in breast cancer," *Med. Sci. Res.*, 21: 383-384 (1993;.

(Continued)

*Primary Examiner*—Christopher H. Yaen
(74) *Attorney, Agent, or Firm*—Leona L. Lauder; Joan C. Harland

(57) ABSTRACT

Disclosed are methods and compositions for identifying malignant tumors that overexpress the c-erbB-2 oncogene. Assays useful for diagnosis and prognosis of neoplastic disease are provided which detect the external domain of c-erbB-2, the glycoprotein gp75 and quantitate the level of gp75 in the biological fluids of mammals carrying a tumor burden.

Further disclosed are recombinant, synthetically and otherwise biologically produced novel proteins and polypeptides which are encoded by the external domain DNA sequence of the c-erbB-2 oncogene (the gp75 gene) or fragments thereof. Such gp75 proteins and polypeptides are useful as vaccines, therapeutically in the treatment of cancer either alone or in combination with chemotherapeutic agents.

Also disclosed are antibodies to such gp75 proteins and polypeptides which are useful diagnostically and therapeutically. Still further disclosed are test kits embodying the assays of this invention.

74 Claims, 17 Drawing Sheets

OTHER PUBLICATIONS

Chiba et al., "Growth-associated Shedding of a Tumor Antigen (CE7) Detected by a Monoclonal Antibody", *Cancer Research*, 49: 3972-3975 (Jul. 18, 1989).

Coussens et al., "Tyrosine Kinase Receptor with Extensive Homology to EGF Receptor Shares Chromosomal Location with *neu*Oncogene", *Science*, 230: 1132-1139 (Dec. 6, 1985).

Di Fiore et al., "erbB-2 is a Potent Oncogene When Overexpressed in NIH/3T3 Cells", *Science*, 237: 178-182 (1987).

Drebin et al., "Down-Modulation of an Oncogene Protein Product and Reversion of the Transformed Phenotype by Monoclonal Antibodies", *Cell*, 41: 695-706 (1985).

Drebin et al., "Inhibition of tumor growth by a monoclonal antibody reactive with an oncogene-encoded tumor antigen," *PNAS* (USA) 83: 9129-9133 (Dec. 1986).

Gullick et al., "Expression of the c-*erbB*-2 Protein in Normal and Transformed Cells," *Int. J. Cancer, 40:* 246-254 (1987).

Hudziak et al., "p185$^{HER2}$ Monoclonal Antibody Has Antiproliferative Effects In Vitro and Sensitizes Human Breast Tumor Cells to Tumor Necrosis Factor", *Mol. Cell. Biol.*, 9(3): 1165-1172 (1989).

Hung et al., "Molecular cloning of the *neu* gene: Absence of gross structural alteration in oncogenic alleles", *PNAS* (USA), 83: 261-264 (1986).

Iacobelli et al., "Detection of Antigens Recognized by a Novel Monoclonal Antibody in Tissue and Serum from Patients with Breast Cancer", *Cancer Research*, 46: 3005-3010 (1986).

Isola et al., "Elevated *erb*B-2 Oncoprotein Levels in Preoperative and Follow-up Serum Samples Define an Aggressive Disease Course in Patients with Breast Cancer," *Cancer, 73(3):* 653-658 (Feb. 1, 1994).

King et al., "Amplification of a Novel v-*erb*B-Related Gene in a Human Mammary Carcinoma", *Science*, 229: 972-974 (Dec. 1985).

Langton et al., "The development and characterization of antibodies to different regions of the c-erbB-2 protein on breast tumor tissue and cell lines" (Abstract and Poster), presented at the 1989 American Association for Cancer Research Conference (May 24-27, 1989).

Loughnan et al., "Soluble interleukin 2 receptors are released from the cell surface of normal murine B lymphocytes stimulated with interleukin 5," *PNAS* (USA), 85: 3115-3119 (19880.

Maguire and Greene, "The *neu* (c-erbB-2) Oncogene," *Seminars in Oncology*, 16 (2): 148-155 (Apr. 1989).

McCann et al., "c-erbB-2 Oncoprotein Expression in Malignant and Nonmalignant Breast Tissue," *I.J.M.S.*, 158 (6): 137-140 (Jun. 1989).

Merlino, et al., "Amplification and Enhanced Expression of the Epiderman Growth Factor Receptor Gene in A431 Human Carcinoma Cells," *Science*, 224: 417-419 (1984).

Myones et al., "Identification of a Spontaneously Shed Fragment of B Cell Complement Receptor Type Two (CR2) Containing the C3d-Binding Site", *Complement*, 4: 87-98 (1987).

Price et al., "The Production and Characterisation of Monoclonal Antibodies to myc, c-erb-B-2 and EGF-receptor Using a Synthetic Peptide Approach", [Symposium on Monoclonal Antibodies for Therapy, Prevention and in vitro Diagnosis of Human Disease, (Ulrecht, The Netherlands; May 17-19, 1989)] *Develop. Biol. Standarad*, 71: 23-31 (1990).

Ring et al., "Distribution and Physical Properties of BCA200, a M 200,000 Glycoprotein Selectively Associated with Human Breast Cancer", *Cancer Research*, 49: 3070-3080 (1989).

Sainsbury et al., "Epidermal-Growth-Factor Receptor Status as Predictor of Early Recurrence of and Death from Breast Cancer", *The Lancet:* 1398-1402 (Jun. 20, 1987).

Schechter, et al., The *neu* Gene: An erbB-Homologous Gene Distinct from and Unlinked to the Gene Encoding the EGF Receptor, *Science*, 229: 976-978 (1985).

Setton et al., "*neus* about c-*erb*-B-2 and HER2", *TIG*, 4: 247-248 (1988).

Semba et al., "A v-erbB-related protoonocogene, c-erbB-2, is distinct from the c-erB-1/epidermal growth factor-receptor gene and is amplified in a human salivary gland adenocarcinoma", *PNAS* (USA), 82: 6497-6501 (1985).

Slamon et al., "Human Breast Cancer: Correlation or Relapse and Survival with Amplification of HER-2/neu Oncogene", *Science*, 235: 177-182 (1987).

Slamon et al., "Studies of the HER-2/neu Proto-oncogene in Human Breast and Ovarian Cancer", *Science*, 244: 707-712 (1989).

Tuzi et al., "Production and characterization of monoclonal antibodies to the c-erbB-2 proto-oncogene protein using a synthetic pepetide immunogen", *Biochemical Society Transactions* 65th Meeting, London (1988).

Ullrich et al., "Human Epidermal Growth Factor Receptor CDNA Sequence and Aberrant Expression of the Amplified Gene in A431 Epidermoid Carcinoma Cells", *Nature*. 309: 418-425 (May 31, 1984).

Varley et al., "Alterations to either c-*erbB*-2 (neu) or c-*myc*protooncogenes in breast carcinomas correlate with poor short-term prognosis," *Oncogen*.1: 423-430 (1987).

Weber et al., "Production of an Epidermal Growth Factor Receptor Related Protein", *Science*. 224: 294-297 (Apr. 20, 1984).

Weber and Keeney, "Medium-Scale Ligand-Affinity Purification of Two Soluble Forms of Human Interleukin-2 Receptor", *Journal of Chromatography*, 431: 55-63 (1988).

Wu et al., "Detection of the Extracellular Domain of c-*erbB*-2 Oncoprotein in Sera From Patients With Various Carcinomas: Correlation With Tumor Markers", *Journal of Clincal Laboratory Analysis*. 7: 31-40 (1993).

Yamamoto et al., "Similarity of protein encoded by the human c-*erb*-B-2 gene to epidermal growth factor receptor," *Nature*319: 230-234 (Jan. 16, 1986).

Yarden and Weinberg, "Experimental approaches to hypothetical hormones: Detection of a candidate ligand of the new protonocogene," *PNAS* (USA) 86: 3179-3183 (May 1989).

* cited by examiner

```
  1    AATTCTCGAGCTCGTCGACCGGTCGACGAGCTCGAGGGTCGACGAGC
       1                                            10
       MetGluLeuAlaAlaLeuCysArgTrpGlyLeuLeuLeuAlaLeuLe
151    ATGGAGCTGGCGGCCTTSTGCCGCTGGGGGCTCCTCCTCGCCCTCTT
                                 60
       GlnGlyCysGlnValValGlnGlyAsnLeuGluLeuThrTyrLeuPr
301    CAGGGCTGCCAGGTGGTGCAGGGAAACCTGGAACTCACCTACCTGCC
                                110
       IleValArgGlyThrGlnLeuPheGluAspAsnTyrAlaLeuAlaVa
451    ATTGTGCGAGGCACCCAGCTCTTTGAGGACAACTATGCCCTGGCCGT
                                160
       GlyGlyValLeuIleGlnArgAsnProGlnLeuCysTyrGlnAspTh
601    GGAGGGGTCTTGATCCAGCGGAACCCCCAGCTCTGCTACCAGGACAC
                                210
       GlySerArgCysTrpGlyGluSerSerGluAspCysGlnSerLeuTh
751    GGCTCCCGCTGCTGGGGAGAGAGTTCTGAGGATTGTCAGAGCCTGAC
                                260
       AspCysLeuAlaCysLeuHisPheAsnHisSerGlyIleCysGluLe
901    GACTGCCTGGCCTGCCTCCACTTCAACCACAGTGGCATCTGTGAGCT
                                310
       TyrAsnTyrLeuSerThrAspValGlySerCysThrLeuValCysPr
1051   TACAACTACCTTTCTACGGACGTGGGATCCTGCACCCTCGTCTGCCC
                                360
       ArgGluValArgAlaValThrSerAlaAsnIleGlnGluPheAlaGl
1201   CGAGAGGTGAGGGCAGTTACCAGTGCCAATATCCAGGAGTTTGCTGG
                                410
       GluThrLeuGluGluIleThrGlyTyrLeuTyrIleSerAlaTrpPr
1351   GAGACTCTGGAAGAGATCACAGGTTACCTATACATCTCAGCATGGCC
                                460
       SerTrpLeuGlyLeuArgSerLeuArgGluLeuGlySerGlyLeuAl
1501   AGCTGGCTGGGGCTGCGCTCACTGAGGGAACTGGGCAGTGGACTGGC
                                510
       GluAspGluCysValGlyGluGlyLeuAlaCysHisGlnLeuCysAl
1651   GAGGACGAGTGTGTGGGCGAGGGCCTGGCCTGCCACCAGCTGTGCGC
                                560
       ProArgGluTyrValAsnAlaArgHisCysLeuProCysHisProGl
1801   CCCAGGGAGTATGTGAATGCCAGGCACTGTTTGCCGTGCCACCCTGA
                                610
       ProSerGlyValLysProAspLeuSerTyrMetProIleTrpLysPh
1951   CCCAGCGGTGTGAAACCTGACCTCTCCTACATGCCCATCTGGAAGTT
```

*FIG. 16A*

```
              TCGAGGGCGCGCGCCCGGCCCCCACCCCTCGCAGCACCCCGCGCCCCGC
                        20                              30
           uProProGlyAlaAlaSerThrGlnVal|Cys|ThrGlyThrAspMetLysLe
           GCCCCCCGGAGCCGCGAGCACCCAAGT|GTGC|ACCGGCACAGACATGAAGCT
                       70                        80
            oThrAsnAlaSerLeuSerPheLeuGlnAspIleGlnGluValGlnGlyTy
            CACCAATGCCAGCCTGTCCTTCCTGCAGGATATCCAGGAGGTGCAGGGCTA
                       120                            130
            lLeuAspAsnGlyAspProLeuAsnAsnThrThrProValThrGlyAlaSe
            GCTAGACAATGGAGACCCGCTGAACAATACCACCCCTGTCACAGGGGCCTC
                       170                        180
            rIleLeuTrpLysAspIlePheHisLysAsnAsnGlnLeuAlaLeuThrLe
            GATTTTGTGGAAGGACATCTTCCACAAGAACAACCAGCTGGCTCTCACACT
                        220                             230
           rArgThrVal|Cys|AlaGlyGly|Cys|AlaArg|Cys|LysGlyProLeuProTh
           GCGCACTGTC|TGT|GCCGGTGGC|TGT|GCCCGC|TGC|AAGGGGCCACTGCCCAC
                       270                          280
            uHis|Cys|ProAlaLeuValThrTyrAsnThrAspThrPheGluSerMetPr
            GCAC|TGC|CCAGCCCTGGTCACCTACAACACAGACACGTTTGAGTCCATGCC
                       320                             330
            oLeuHisAsnGlnGluValThrAlaGluAspGlyThrGlnArg|Cys|GluLy
            CCTGCACAACCAAGAGGTGACAGCAGAGGATGGAACACAGCGG|TGT|GAGAA
                       370                       380
           y|Cys|LysLysIlePheGlySerLeuAlaPheLeuProGluSerPheAspGl
           C|TGC|AAGAAGATCTTTGGGAGCCTGGCATTTCTGCCGGAGAGCTTTGATGG
                       420                       430
            oAspSerLeuProAspLeuSerValPheGlnAsnLeuGlnValIleArgGl
            GGACAGCCTGCCTGACCTCAGCGTCTTCCAGAACCTGCAAGTAATCCGGGG
                       470                        480
           aLeuIleHisHisAsnThrHisLeu|Cys|PheValHisThrValProTrpAs
           CCTCATCCACCATAACACCCACCTC|TGC|TTCGTGCACACGGTGCCCTGGGA
                       520                         530
            aArgArgAlaLeuLeuGlySerGlyProThrGln|Cys|ValAsn|Cys|SerGl
            CCGCAGGGCACTGCTGGGGTCAGGGCCCACCCA|GTGT|GTCAAC|TGC|AGCCA
                       570                        580
           u|Cys|GlnProGlnAsnGlySerValThr|Cys|PheGlyProGluAlaAspGl
           G|TGT|CAGCCCCAGAATGGCTCAGTGACC|TGT|TTTGGACCGGAGGCTGACCA
                       620                          630
            eProAspGluGluGlyAla|Cys|GlnPro|Cys|ProIleAsn|Cys|ThrHisSe
            TCCAGATGAGGAGGGCGCA|TGC|CAGCCT|TGC|CCCATCAAC|TGC|ACCCACTC
```

FIG. 16B

```
          CCTCCCAGCCGGGTCCAGCCGGAGCCATGGGGCCGGAGCCGCAGTGAGCACC
                           40                           50
        uArgLeuProAlaSerProGluThrHisLeuAspMetLeuArgHisLeuTyr
          GCGGCTCCCTGCCAGTCCCGAGACCCACCTGGACATGCTCCGCCACCTCTAC
                           90                          100
        rValLeuIleAlaHisAsnGlnValArgGlnValProLeuGlnArgLeuArg
          CGTGCTCATCGCTCACAACCAAGTGAGGCAGGTCCCACTGCAGAGGCTGCGG
                          140                          150
        rProGlyGlyLeuArgGluLeuGlnLeuArgSerLeuThrGluIleLeuLys
          CCCAGGAGGCCTGCGGGAGCTGCAGCTTCGAAGCCTCACAGAGATCTTGAAA
                          190                          200
        uIleAspThrAsnArgSerArgAlaCysHisProCysSerProMetCysLys
          GATAGACACCAACCGCTCTCGGGCCTGCCACCCCTGTTCTCCGATGTGTAAG
                          240                          250
        rAspCysCysHisGluGlnCysAlaAlaGlyCysThrGlyProLysHisSer
          TGACTGCTGCCATGAGCAGTGTGCTGCCGGCTGCACGGGCCCCAAGCACTCT
                          290                          300
        oAsnProGluGlyArgTyrThrPheGlyAlaSerCysValThrAlaCysPro
          CAATCCCGAGGGCCGGTATACATTCGGCGCCAGCTGTGTGACTGCCTGTCCC
                          340                          350
        sCysSerLysProCysAlaArgValCysTyrGlyLeuGlyMetGluHisLeu
          GTGCAGCAAGCCCTGTGCCCGAGTGTGCTATGGTCTGGGCATGGAGCACTTG
                          390                          400
        yAspProAlaSerAsnThrAlaProLeuGlnProGluGlnLeuGlnValPhe
          GGACCCAGCCTCCAACACTGCCCCGCTCCAGCCAGAGCAGCTCCAAGTGTTT
                          440                          450
        yArgIleLeuHisAsnGlyAlaTyrSerLeuThrLeuGlnGlyLeuGlyIle
          ACGAATTCTGCACAATGGCGCCTACTCGCTGACCCTGCAAGGGCTGGGCATC
                          490                          500
        pGlnLeuPheArgAsnProHisGlnAlaLeuLeuHisThrAlaAsnArgPro
          CCAGCTCTTTCGGAACCCGCACCAAGCTCTGCTCCACACTGCCAACCGGCCA
                          540                          550
        nPheLeuArgGlyGlnGluCysValGluGluCysArgValLeuGlnGlyLeu
          GTTCCTTCGGGGCCAGGAGTGCGTGGAGGAATGCCGAGTACTGCAGGGGCTC
                          590                          600
        nCysValAlaCysAlaHisTyrLysAspProProPheCysValAlaArgCys
          GTGTGTGGCCTGTGCCCACTATAAGGACCCTCCCTTCTGCGTGGCCCGCTGC
                          640                          650
        rCysValAspLeuAspAspLysGlyCysProAlaGluGlnArgAlaSerPro
          CTGTGTGGACCTGGATGACAAGGGCTGCCCCGCCGAGCAGAGAGCCAGCCCT
               ↓
```

FIG. 16C

```
                            660
      LeuThrSer IleValSerAlaValGlyIleLeuLeuValVa
2101  CTGACGTCC ATCGTCTCTGCGGTGGTTGGCATTCTGCTGGTCGTGGT
                           710
      ThrProSerGlyAlaMetProAsnGlnAlaGlnMetArgIleLeuLy
2251  ACACCTAGCGGAGCGATGCCCAACCAGGCGCAGATGCGGATCCTGAA
                          760
      AlaIleLysValLeuArgGluAsnThrSerProLysAlaAsnLysGl
2401  GCCATCAAAGTGTTGAGGGAAAACACATCCCCCAAAGCCAACAAAGA
                           810
      MetProTyrGly CysLeuLeuAspHisValArgGluAsnArgGlyAr
2551  ATGCCCTATGGC TGC CTCTTAGACCATGTCCGGGAAAACCGCGGACG
                           860
      ValLeuValLysSerProAsnHisValLysIleThrAspPheGlyLe
2701  GTGCTGGTCAAGAGTCCCAACCATGTCAAAATTACAGACTTCGGGCT
                           910
      HisGlnSerAspValTrpSerTyrGlyValThrValTrpGluLeuMe
2851  CACCAGAGTGATGTGTGGAGTTATGGTGTGACTGTGTGGGAGCTGAT
                           △
      ValTyrMetIleMetValLys Cys TrpMetIleAspSerGlu Cys Ar
3001  GTCTACATGATCATGGTCAAA TGT TGGATGATTGACTCTGAA TGT CG
                          1010
      AspSerThrPheTyrArgSerLeuLeuGluAspAspAspMetGlyAs
3151  GACAGCACCTTCTACCGCTCACTGCTGGAGGACGATGACATGGGGGA
                          1060
      SerThrArgSerGlyGlyGlyAspLeuThrLeuGlyLeuGluProSe
3301  TCTACCAGGAGTGGCGGTGGGGACCTGACACTAGGGCTGGAGCCCTC
                          1110
      LeuProThrHisAspProSerProLeuGlnArgTyrSerGluAspPr
3451  CTCCCCACACATGACCCCAGCCCTCTACAGCGGTACAGTGAGGACCC
                          1160
      SerProArgGluGlyProLeuProAlaAlaArgProAlaGlyAlaTh
3601  TCGCCCCGAGAGGGCCCTCTGCCTGCTGCCCGACCTGCTGGTGCCAC
                          1210
      GlyGlyAlaAlaProGlnProHisProProProAlaPheSerProAl
3751  GGAGGAGCTGCCCCTCAGCCCCACCCTCCTCCTGCCTTCAGCCCAGC
                          1255
      LeuAspValProValEND
3901  CTGGACGTGCCAGTGTGAACCAGAAGGCCAAGTCCGCAGAAGCCCTG
4051  CTAAGGAACCTTCCTTCCTGCTTGAGTTCCCAGATGGCTGGAAGGGG
4201  CCCTTTCCTTCCAGATCCTGGGTACTGAAAGCCTTAGGGAAGCTGGC
4351  ATGGTGTCAGTATCCAGGCTTTGTACAGAGTGCTTTTCTGTTTAGTT
4501  TTGTCCATTTGCAAATATATTTTGGAAAACAAAAAAAAAAAAAA
```

FIG. 16D

```
        670                           680
lLeuGlyValValPheGlyIleLeuIleLysArgArgGlnGlnLysIleAr
CTTGGGGGTGGTCTTTGGGATCCTCATCAAGCGACGGCAGCAGAAGATCCG
        720                           730
sGluThrGluLeuArgLysValLysValLeuGlySerGlyAlaPheGlyTh
AGAGACGGAGCTGAGGAAGGTGAAGGTGCTTGGATCTGGCGCTTTTGGCAC
        770                           780
uIleLeuAspGluAlaTyrValMetAlaGlyValGlySerProTyrValSe
AATCTTAGACGAAGCATACGTGATGGCTGGTGTGGGCTCCCCATATGTCTC
                                      830
gLeuGlySerGlnAspLeuLeuAsnTrpCysMetGlnIleAlaLysGlyMe
CCTGGGCTCCCAGGACCTGCTGAACTGGTGTATGCAGATTGCCAAGGGGAT
        870                           880
uAlaArgLeuLeuAspIleAspGluThrGluTyrHisAlaAspGlyGlyLy
GGCTCGGCTGCTGGACATTGACGAGACAGAGTACCATGCAGATGGGGGCAA
        920                           930
tThrPheGlyAlaLysProTyrAspGlyIleProAlaArgGluIleProAs
GACTTTTGGGGCCAAACCTTACGATGGGATCCCAGCCCGGGAGATCCCTGA
        970                           980
gProArgPheArgGluLeuValSerGluPheSerArgMetAlaArgAspPr
GCCAAGATTCCGGGAGTTGGTGTCTGAATTCTCCCGCATGGCCAGGGACCC
       1020                          1030
pLeuValAspAlaGluGluTyrLeuValProGlnGlnGlyPhePheCysPr
CCTGGTGGATGCTGAGGAGTATCTGGTACCCCAGCAGGGCTTCTTCTGTCC
       1070                          1080
rGluGluGluAlaProArgSerProLeuAlaProSerGluGlyAlaGlySe
TGAAGAGGAGGCCCCCAGGTCTCCACTGGCACCCTCCGAAGGGGCTGGCTC
       1120                          1130
oThrValProLeuProSerGluThrAspGlyTyrValAlaProLeuThrCy
CACAGTACCCCTGCCCTCTGAGACTGATGGCTACGTTGCCCCCCTGACCTG
       1170                          1180
rLeuGluArgAlaLysThrLeuSerProGlyLysAsnGlyValValLysAs
TCTGGAAAGGGCCAAGACTCTCTCCCCAGGGAAGAATGGGGTCGTCAAAGA
       1220                          1230
aPheAspAsnLeuTyrTyrTrpAspGlnAspProProGluArgGlyAlaPr
CTTCGACAACCTCTATTACTGGGACCAGGACCCACCAGAGCGGGGGGCTCC

ATGTGTCCTCAGGGAGCAGGGAAGGCCTGACTTCTGCTGGCATCAAGAGGT
TCCAGCCTCGTTGGAAGAGGAACAGCACTGGGGAGTCTTTGTGGATTCTGA
CTGAGAGGGGAAGCGGCCCTAAGGGAGTGTCTAAGAACAAAAGCGACCCAT
TTTACTTTTTTTGTTTTGTTTTTTTAAAGACGAAATAAAGACCCAGGGGAG
```

FIG. 16E

```
              690                              700
    gLysTyrThrMetArgArgLeuLeuGlnGluThrGluLeuValGluProLeu
    GAAGTACACGATGCGGAGACTGCTGCAGGAAACGGAGCTGGTGGAGCCGCTG
              740                              750
    rValTyrLysGlyIleTrpIleProAspGlyGluAsnValLysIleProVal
    AGTCTACAAGGGCATCTGGATCCCTGATGGGGAGAATGTGAAAATTCCAGTG
              790                              800
    rArgLeuLeuGlyIleCysLeuThrSerThrValGlnLeuValThrGlnLeu
    CCGCCTTCTGGGCATCTGCCTGACATCCACGGTGCAGCTGGTGACACAGCTT
              840                              850
    tSerTyrLeuGluAspValArgLeuValHisArgAspLeuAlaAlaArgAsn
    GAGCTACCTGGAGGATGTGCGGCTCGTACACAGGGACTTGGCCGCTCGGAAC
              890                              900
    sValProIleLysTrpMetAlaLeuGluSerIleLeuArgArgArgPheThr
    GGTGCCCATCAAGTGGATGGCGCTGGAGTCCATTCTCCGCCGGCGGTTCACC
    △         940                              950
    pLeuLeuGluLysGlyGluArgLeuProGlnProProIleCysThrIleAsp
    CCTGCTGGAAAAGGGGGAGCGGCTGCCCCAGCCCCCCATCTGCACCATTGAT
              990                              1000
    oGlnArgPheValValIleGlnAsnGluAspLeuGlyProAlaSerProLeu
    CCAGCGCTTTGTGGTCATCCAGAATGAGGACTTGGGCCCAGCCAGTCCCTTG
              1040                             1050
    oAspProAlaProGlyAlaGlyGlyMetValHisHisArgHisArgSerSer
    AGACCCTGCCCCGGGCGCTGGGGGCATGGTCCACCACAGGCACCGCAGCTCA
              1090                             1100
    rAspValPheAspGlyAspLeuGlyMetGlyAlaAlaLysGlyLeuGlnSer
    CGATGTATTTGATGGTGACCTGGGAATGGGGGCAGCCAAGGGGCTGCAAAGC
              1140                             1150
    sSerProGlnProGluTyrValAsnGlnProAspValArgProGlnProPro
    CAGCCCCCAGCCTGAATATGTGAACCAGCCAGATGTTCGGCCCCAGCCCCCT
              1190                             1200
    pValPheAlaPheGlyGlyAlaValGluAsnProGluTyrLeuThrProGln
    CGTTTTTGCCTTTGGGGGTGCCGTGGAGAACCCCGAGTACTTGACACCCCAG
              1240                    ▽        1250
    oProSerThrPheLysGlyThrProThrAlaGluAsnProGluTyrLeuGly
    ACCCAGCACCTTCAAAGGGACACCTACGGCAGAGAACCCAGAGTACCTGGGT

GGGAGGGCCCTCCGACCACTTCCAGGGGAACCTGCCATGCCAGGAACCTGTC
    GGCCCTGCCCAATGAGACTCTAGGGTCCAGTGGATGCCACAGCCCAGCTTGG
    TCAGAGACTGTCCCTGAAACCTAGTACTGCCCCCCATGAGGAAGGAACAGCA
    AATGGGTGTTGTATGGGGAGGCAAGTGTGGGGGGTCCTTCTCCACACCCACT
```

*FIG. 16F*

C-ERBB-2 EXTERNAL DOMAIN: GP75

This application is a continuation of U.S. Ser. No. 07/968,059 filed on Oct. 28, 1992, now abandoned which is a divisional of U.S. Ser. No. 07/826,231 filed Jan. 22, 1992, now abandoned, which is a file wrapper continuation application of U.S. Ser. No. 07/389,920 filed Aug. 4, 1989, now abandoned. This application claims priority in said prior filed applications.

FIELD OF THE INVENTION

This invention is in the fields of biochemical engineering and immunochemistry. More particularly, this invention relates to recombinant DNA molecules expressed in appropriate host organisms as well as novel proteins and polypeptide fragments thereof which can be produced recombinantly, synthetically or by other means, such as, the fragmentation of biologically produced proteins and polypeptides. The recombinant DNA molecules of this invention are characterized by the DNA which codes for proteins and polypeptides from the external domain of the c-erbB-2 oncogene which is herein designated glycoprotein 75 (gp75). The serologically active, immunogenic and/or antigenic proteins and polypeptides are useful as reagents for the immunological detection of gp75 in the body fluids of cancer patients enabling a diagnostician to make important judgements about the status and prognosis of the patients, and for the production of antibodies and for affinity purification. Central to this invention are diagnostic assays designed to detect gp75 in body fluids of mammals. The expressed or synthetically or biologically produced proteins and polypeptides of this invention are further useful as vaccines for enhancing the immunological responses of cancer patients to tumorigenic activity and of recovered cancer patients to subsequent tumorigenic challenge. Still further, said gp75 proteins and polypeptides are useful therapeutically in dampening the tumorigenic activity of c-erbB-2 expressing cells.

BACKGROUND OF THE INVENTION

The mechanism for malignancy of mammalian cells has been and continues to be the subject of intense investigation. One of the most promising areas is the elucidation of how oncogenes are turned on and turned off. A number of oncogenes have been shown to play an important role in causing cancer. The proteins encoded by oncogenes function abnormally and seem to play a part in ordaining the transformation of a normal cell into a cancer cell. Oncogenes were first detected in retroviruses, and then cellular counterparts of the viral oncogenes were found. A retroviral gene responsible for rapid oncogenesis was first identified in the early 1970's in Rous sarcoma virus (RSV), which causes cancer in chickens; the gene was named src, for sarcoma. In 1975, it was found that the viral src gene (v-src) has a nearly exact copy in all chicken cells; the cellular counterpart of v-src is c-src.

A score of oncogenes have since been isolated from retroviruses that variously cause carcinoma, sarcoma, leukemia or lymphoma in chickens, other birds, rats, mice, cats or monkeys. In each case, the oncogene has been found to be closely related to a normal gene in the host animal and to encode an oncogenic protein similar to a normal protein.

Oncogenes were also discovered in human and animal tissues. Genes in the DNA of various kinds of tumor cells, when introduced by transfection into normal cultured cells, transform them into cancer cells. Such oncogenes are also virtual copies of proto-oncogenes. Whatever the specific mechanism converting a proto-oncogene into an oncogene may be, an oncogene exerts its effect by way of the protein it encodes. The products of the proto-oncogenes from which oncogenes are derived appear to have roles that are critical in the regulation of cell growth and differentiation and in embryonic development. Transforming proteins may have their profound effects on cells because they disturb these fundamental cellular processes.

Enzymatic activity in catalyzing the addition of a phosphate molecule to an amino acid (phosphorylation) is known to be important in the control of protein function. The enzymes that phosphorylate proteins are called protein kinases (from the Greek kinein, "to move"). Almost one-third of all the known oncogenes code for protein kinases specific for tyrosine residues.

Epidermal growth factor (EGF) and platelet-derived growth factor (PDGF), when added to a culture of nondividing cells, stimulate the cells to divide. EGF and PDGF deliver their signal by binding to specific protein receptors embedded in the cell's plasma membrane. When the receptor protein for EGF was isolated, it was found to be associated with tyrosine kinase activity, which is stimulated when an EGF molecule binds to the receptor. The PDGF receptor was then shown to have similar enzymatic function.

A human proto-oncogene having tyrosine kinase activity was identified by three research groups: Semba et al., *PNAS(USA)*, 82: 6497 (1984) (designating the gene c-erbB-2); Coussens et al., *Science*, 230:1132 (1985) (designating the gene HER2); and King et al., *Science*, 229:974 (1985) (designating the gene MAC117). A related rat gene (designated neu) was reported by Schecter et al., *Science*, 229:976 (1985). Amplification of the gene and/or increased translation of expression of the gene has been observed in tumor cells and cell lines. [See, for example, Fukushige et al., *Mol. Cell. Biol.*, 6:955 (1986) where amplification and elevated expression (mRNA) of the gene were observed in the MKN-7 gastric cell line; Coussens et al., supra, where elevated transcription of the gene was observed in cell lines from a hepatoblastoma, a Ewing sarcoma, a rhabdomyosarcoma, two neuroblastomas, and a Wilms tumor; Semba et al., supra, where the gene was observed to be amplified in a human salivary gland adenocarcinoma; King et al., supra, where amplification was observed in a mammary carcinoma cell line; Yokota et al., *Lancet, 1*:756 (1986) where amplification of the gene was observed in breast, kidney and stomach adenocarcinomas; and Tal et al., *Cancer Res.*, 48:1517 (1988) where sporadic amplification of the gene was found in adenocarcinomas of various tissues.]

The c-erbB-2 receptor is closely related to but distinct from the EGF receptor. Like the EGF receptor, the c-erbB-2 protein has an extracellular domain, a transmembrane domain that includes two cysteine-rich repeat clusters, and an intracellular kinase domain; but the c-erbB-2 protein has a molecular weight of 185,000 daltons (185 kd) whereas the EGF receptor has a molecular weight of about 170 k [Schechter et al., *Nature*, 312:513 (1984)]. Hunter, *Sci. Am.*, 251: 70 at 77 (1984), postulates that the c-erbB-2 protein (gp185) mimics the tyrosine kinase action of the EGF receptor but in an unregulated way.

Tyrosine kinases can be divided into two functional groups: those in which the product of the c-src gene is a prototype, and those that function as cell surface receptors. At least twelve mammalian tyrosine kinases have been identified as being associated with cellular growth factors or their receptors. Three of these oncogenes share strong homology with growth factors [c-sis with platelet-derived growth factor (PDGF), hst and int2 with fibroblast growth factor (FGF)]. Others share strong homology with the growth factor receptors [c-erbB with the epidermal growth factor (EGF) receptor, fms with the colony-stimulating factor (CSF-1) receptor] for which ligands have been identified. The remaining seven, namely eph, c-erbB-2, c-kit, met, ret, c-ros, and trk, may be receptors with ligands, but to date the ligands have not been identified.

There is now mounting evidence that some cells become tumorigenic due to alterations in their cell surface receptors. These alterations can consist of genetic rearrangements, point mutations, or gene amplifications evident at the DNA, RNA, or protein level [Drebin et al., Oncogene, 2:387 (1988); Bargmann et al., Cell, 45:649 (1986); Der, Clin. Chem., 33:641 (1987)]. Although some of the above-referenced receptors are present on the surface of normal cells, the overexpression of certain oncogenes has been shown to correlate with tumorigenic activity; such is the case of c-erbB-2.

It has now been observed that the c-erbB-2 oncogene, which is capable of transforming cells to malignancy, is present in some tumors at very high levels [Zhou et al., Cancer Research, 47:6123 (1987); Berger et al., Cancer Research, 48:1238 (1988); Kraus et al., The EMBO Journal, 6(3):605 (1987); and Slamon et al., Science, 235:177 (1987)]. The expression of the c-erbB-2 oncogene, and its location in the external membrane of cells appears to be closely associated with cancer [Kraus et al., id; Slamon et al., id; Drebin et al., Cell, 41:695 (1985); and Di Fiore et al., Science, 237:178 (1987)]; it may, in fact, be the primary event in the development of cancer in at least some cases [Muller et al., Cell, 54:105 (1988)]. Overexpression of the c-erbB-2 protein on the surface of normal cells appears to cause them to be transformed or otherwise behave as tumor cells. [Drebin et al., supra; Di Fiore et al., supra; and Hudziak et al., PNAS (USA), 84:7159 (1987).]

Further, patients with high levels of expression of the c-erbB-2 oncogene have been shown to have a very poor clinical prognosis [Slamon et al., Science, 235:177 (1987)]. This correlation between the overexpression of c-erbB-2 and a poor prognosis can yield information of both diagnostic and prognostic value [Kraus et al., The EMBO Journal, 6:605 (1987); and Slamon et al., id]. A decision on the extent of clinical therapy required by the patient can be made based on the ability to detect overexpression of the c-erbB-2 oncogene or protein.

Antibodies can be used to detect c-erbB-2 expressed in tumor tissues by tissue slice evaluation or histopathology. The methodology has demonstrated that useful prognostic indications can be achieved [van de Vijver et al., Mol. and Cell Biol., 7:2019 (1987); Zhou et al., Cancer Res., 47:6123 (1987); Berger et al., Cancer Res., 48:1238 (1988); Kraus et al., supra (1987); and Slamon et al., supra]. There are, however, many cases in which tissue is not readily available or in which it is not desirable or not possible to withdraw tissue from tumors. Therefore, there is a need in the medical art for rapid, accurate diagnostic tests that are convenient and non-traumatic to patients. The invention claimed herein meets said need by providing for non-invasive diagnostic assays to detect overexpression of c-erbB-2 in mammals.

Smith et al., Science, 238:1704 (1987), reported that excess of a soluble membrane receptor (CD4 antigen) blocks HIV-1 infectivity.

Soluble, secreted forms of CD4 were produced by transfection of mammalian cells with vectors encoding versions of CD4 lacking its transmembrane and cytoplasmic domains. The soluble CD4 produced is reported to bind HIV-1's envelope glycoprotein (gp120) with an affinity and specificity comparable to intact CD4.

Weber and Gill, Science 224:294 (1984), reported that human epidermoid carcinoma A431 cells in culture produce a soluble 105 kd protein which they determined to be related to the cell surface domain of the EGF receptor. They further determined that the soluble receptor 105 kd protein was not derived from the membrane-bound intact receptor but separately produced by the cell.

Hearing et al., J. Immunol., 137(1):379 (1986), demonstrated that the immunization of mice with a purified mouse melanoma-specific antigen conferred resistance to subsequent challenge with mouse melanoma cells in a syngeneic host.

Bernards et al., PNAS (USA), 84:6854 (1987), demonstrated that a recombinant vaccinia virus expressing the external domain, the transmembrane anchor domain and about 50 amino acids of the intracellular domain of the rat equivalent of the human c-erbB-2 oncogene, the "neu" oncogene, when used to immunize mice, conveyed protection to a subsequent challenge with neu expressing tumor cells. It is noted therein that the ectodomain (external domain) of the rat neu protein is a highly immunogenic determinant in tumor-bearing mice (strain NFS).

Aaronson et al., NTIS (National Technical Information Service) application entitled "A Human Gene Related to but Distinct from EGF Receptor Gene" (U.S. Pat. No. 6,836, 414; filed Mar. 5, 1986), describes the cloning, isolation and partial characterization of a v-erbB related human gene that is a member of the tyrosine kinase encoding family of genes and is amplified in a human mammary carcinoma. Said gene has been determined to be c-erbB-2. That application describes as objects thereof to provide the following: antibodies directed against the protein product encoded by said gene and a diagnostic kit containing said antibodies for the detection of carcinomas; products encoded by the gene; cDNA clones being able to express the protein in a heterologous vector system; transformed cells or organisms capable of expressing the gene; and nucleic acid probes and/or antibody reagent kits capable of detecting said gene or protein product. Said application further suggests the therapeutic use of antibodies specific for the gene product which have been conjugated to a toxin, and suggests that if a ligand exists for the v-erbB related gene that it also could be used as a targeting agent.

Cline et al., U.S. Pat. No. 4,699,877 (filed Nov. 20, 1984), describes methods and compositions for detecting the presence of tumors, wherein a physiological sample is assayed for the expression product of an oncogene.

Di Fiore et al., Science, 237:178 (1987), notes that a wide variety of human tumors contain an amplified or overexpressed erbB-2 gene. To establish that a ligand-receptor interaction was not required for transformation by the erbB-2 protein, Di Fiore et al. engineered constructs such that sequences encoding the NH2-terminal 621 amino acids (from the external domain) were deleted. Their findings suggested that the NH2-terminal truncation, "if anything, increased the transforming activity of the erbB-2 proteins" (at p. 180).

Aboud-Pirak et al., J. Natl Cancer Inst., 80(20):1605 (1988), reports that monoclonal antibodies against the extracellular domain of the EGF receptor reduced in vitro clone formation of human oral epidermoid carcinoma cells. When the anti-EGF receptor antibodies were added together with cisplatin, the antitumor effect of these agents was shown to be synergistic in vivo.

Berger et al., *Cancer Res.*, 48:1238 (1988), reported that thirteen of 51 DNA samples (25%) from primary human breast tumors contained multiple copies of the c-erbB-2 gene, and observed that there was a statistically significant correlation between c-erbB-2 protein expression and parameters used in breast cancer prognosis (nodal status and nuclear grading). Berger et al. noted that recent studies have shown that c-erbB-2 is amplified in up to 33% of the primary breast tumors examined [King et al., supra; Slamon et al., supra; van de Vijver et al., supra; and Venter et al., *Lancet* 2:69 (1987)] and in up to 25% of human breast cancer cell lines [Kraus et al., supra].

Slamon et al., supra (1987), demonstrated that amplification of the c-erbB-2 gene was correlated with the presence of tumor in the axillary lymph nodes, with estrogen receptor status, and the size of the primary tumor in breast cancer patients. In that study, c-erbB-2 was found to be amplified from 2- to greater than 20-fold in 30% of the 189 primary human breast cancers investigated. Slamon et al. concluded that amplification of the c-erbB-2 gene was a significant predictor of both overall survival and time to relapse in patients with breast cancer. Patients with multiple copies of the gene in DNA from their tumors had a poorer disease outcome with shorter time to relapse as well as a shorter overall survival.

Slamon et al., *Cancer Cells 7/Molecular Diagnostics of Human Cancer*, p. 371 (Cold Spring Harbor Lab. 1989), reported that sequence analysis of several cDNA clones from human breast cancer tumors indicates that, unlike the rat neu gene, mutations in the transmembrane domain may not be an absolute requirement for alteration of the gene product. Instead, the data are consistent with an alteration involving overexpression of a normal product.

Drebin et al., *Cell*, 41:695 (1985), reported that a monoclonal antibody against neu gp185 causes neu-transformed NIH 3T3 cells to revert to a nontransformed phenotype, as evidenced by loss of capacity for anchorage-independent growth. Drebin et al, *Oncogene*, 2:387 (1988), demonstrated that monoclonal antibodies reactive with the cell surface external domains of gp185 can directly inhibit tumor growth in vitro and in vivo.

Masuko et al., *Japn. J. Cancer Res.*, 80:10 (1989), describes a murine IgM monoclonal generated against human c-erbB-2 gene-transfected NIH 3T3 cells, that was reactive with a portion of epithelial tumor cell lines including stomach cancer, colon cancer and liver cancer cell lines, but not with any non-epithelial cell lines.

Yarden and Weinberg, *PNAS(USA)*, 86:3179 (1989), using the neu oncogene as a model system, developed several experimental approaches for the detection of hypothetical ligands for oncogenes encoding transmembrane tyrosine kinases that have structures reminiscent of growth factor receptors. Suggested therein is a candidate ligand of the neu-encoded oncoprotein secreted by fibroblasts upon transformation by ras oncogenes.

The following papers provide a general description of oncogenes, the use of monoclonal antibodies as therapeutic drugs and information about the c-erbB-2 oncogene: Der, *Clin. Chem.*, 33(5):641 (1987); Bishop, *Science*, 235:305 (1987); Henrik and Westermark, *Cell*, 37:9 (1984); Duesberg, *Science*, 228:669 (1985); Shively, *J. Clin. Immunoassay*, 7(1):112 (1984); van de Vijver, *Oncogenes* 2:175 (1988); and Hunter, *Sci. Am*, 251:70 (1984).

SUMMARY OF THE INVENTION

Methods and compositions are provided for identifying malignant tumors that overexpress c-erbB-2. The invention claimed herein is based on the detection of the external domain glycoprotein (gp75) or parts thereof encoded by the c-erbB-2 gene in the biological fluids of mammals carrying a tumor burden. The invention provides for specific diagnostic assays to detect and quantitate gp75 in the biological fluids of mammals, and thereby detect tumors, quantitate their growth, and provide valuable information for the diagnosis and prognosis of neoplastic disease. An elevated level of gp75 in a host's body fluid, that is, above the normal background binding level, is indicative of overexpression of c-erbB-2. (An exemplary background binding level is shown in FIG. 10 as 1.68% for a series of normal human sera.)

The survival of a patient with neoplastic disease, such as breast or ovarian adenocarcinoma among other cancers associated with c-erbB-2 amplification, can be determined by testing a biological fluid from the patient for the presence of gp75 or parts thereof.

Further, this invention provides for assays to detect and quantitate antibodies to gp75 proteins/polypeptides in the body fluids of patients. Such assay results especially in correlation with the results of assays of this invention that determine the level of gp75 proteins/polypeptides in a patient's body fluids provide important information for diagnosing and monitoring the patient's condition deciding upon a course of treatment and in making a prognosis.

Still further, this invention provides for assays to detect and quantitate the level of the putative ligand to gp75 in a patient's body fluid. Similarly such information especially in correlation with the results of assays, herein provided, that detect and quantitate the level of gp75 proteins/polypeptides and antibodies thereto in a patient's body fluids, is of diagnostic and prognostic significance and useful in monitoring the patient's condition and in determining a course of treatment.

As indicated in the Background above, c-erbB-2 amplification has been found to correlate with both a decreased chance of long term survival as well as a shortened time to relapse of the disease. The assays of this invention are useful both pre- and post-operatively. Patients displaying such c-erbB-2 amplification, even at relatively early stages of the disease, may be treated more rigorously in order to increase their chances for survival. Further, the presence of gp75 in a patient's biological fluid after an operation to remove a tumor may indicate metastases requiring immediate intervention, e.g., systemic chemotherapy or radiation therapy.

The present invention fills the need referred to above for non-invasive diagnostic and prognostic assays for the detection of tumors overexpressing c-erbB-2.

Further, this invention is directed to novel proteins and polypeptides encoded by the external domain DNA sequence of the c-erbB-2 oncogene (hereinafter, the gp75 gene) or fragments thereof and to the biochemical engineering of the gp75 gene or fragments thereof into suitable expression vectors; transformation of host organisms with such expression vectors; and production of gp75 proteins and polypeptides by recombinant, synthetic or other biological means. Such recombinant gp75 proteins and polypeptides can be glycosylated or nonglycosylated, preferably glycosylated, and can be purified to substantial purity according to methods described herein. The invention further concerns such gp75 polypeptides and proteins which are synthetically or biologically prepared.

One use of such gp75 proteins and polypeptides is as vaccines. Further, vaccines which effectively provide gp75 epitopes to the immune system can comprise enriched cell membranes that overexpress gp75 or gp185. Such membranes can be derived from recombinant hosts transformed to overexpress c-erbB-2, preferably those overexpressing c-erbB-2 in a form having a truncated internal domain, or from human cancer cell lines. Further useful as vaccines are the anti-idiotype antibodies provided by this invention.

Another use of such gp75 proteins and polypeptides is as therapeutic agents to dampen tumorigenic activity either alone or in combination with chemotherapeutic agents.

A still further use of such gp75 proteins and polypeptides is to detect the putative ligand to c-erbB-2 in affinity binding studies. Should the ligand be so detected in biological fluids of mammals, it may then be purified by the use of the gp75 proteins and polypeptides of this invention; for example, the gp75 proteins and polypeptides may be used in a process to purify the ligand produced by genetic engineering.

Further this invention concerns recombinant DNA molecules comprising a DNA sequence that encodes not only a gp75 protein or polypeptide but also an amino acid sequence of a protein/polypeptide which is not immunogenic to humans and which is not typically reactive to antibodies in human body fluids. An example of such a DNA sequence is the alpha-peptide coding region of beta-galactosidase. Further, claimed herein are such recombinant fused protein/polypeptides which are substantially pure and non naturally occurring.

Further, this invention concerns purified and isolated DNA molecules comprising the gp75 gene or fragments thereof.

A further aspect of this invention relates to the diagnostic and therapeutic use of antibodies to such gp75 proteins and polypeptides. A still further aspect of this invention are anti-idiotype antibodies to such antibodies to gp75 proteins and polypeptides.

A still further aspect of this invention relates to diagnostic assays for gp75 employing the recombinantly, synthetically or otherwise biologically produced gp75 proteins and polypeptides of this invention and/or antibodies thereto.

The invention also provides for test kits that embody the assays of this invention in which test kits comprise antibodies gp75 proteins/polypeptides and/or antibodies to the intact external domain of c-erbB-2 ("intact" herein indicates that the gp75 is expressed on the surface of cells). These assays can be solid phase assays but are not limited thereto, but can also be in a liquid phase format and can be based on ELISAs, particle assays, radiometric or fluorometric assays either unamplified or amplified, using, for example, avidin/biotin technology.

The invention further provides for anti-idiotypes to monoclonal antibodies recognizing gp75 proteins/polypeptides which can substitute for gp75 proteins/polypeptides in the diagnostic assays of this invention.

BRIEF DESCRIPTION OF THE DRAWINGS

FIG. 16 shows the complete nucleotide and amino acid sequences of the c-erbB-2 gene. (Coussens et al. supra.) The gp75 external domain comprises the region from about amino acid number 22 (serine; ser-22) to about amino acid number 653 (serine: ser-653) (said amino acids are marked by black circles above them).

DETAILED DESCRIPTION

Figure 1:
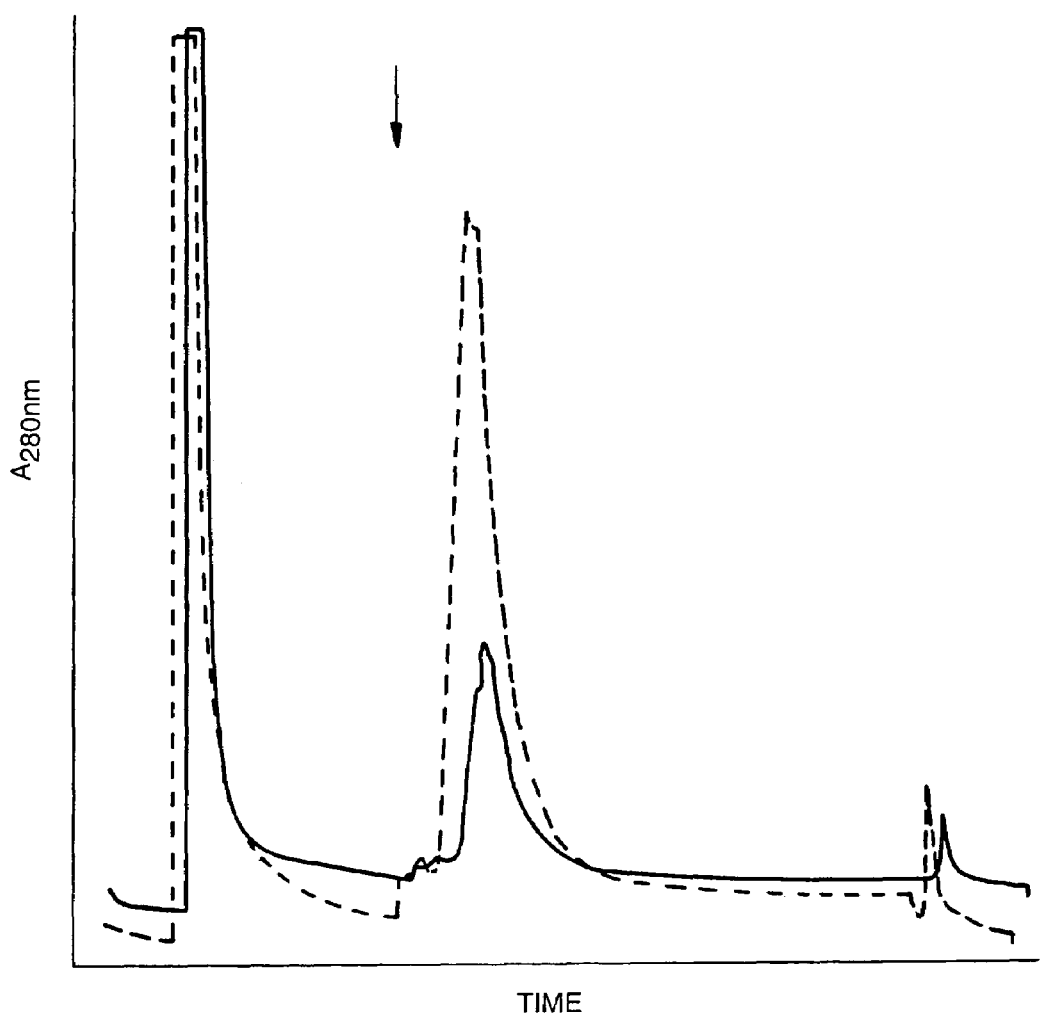
FIG. 1 is an immunoaffinity chromatogram of recombinant c-erbB-2 extracellular domain protein (gp75) expressed from CHO cells. Concentrated CHO supernatant was loaded on the 0.5×5.0 cm immunoaffinity column at a flow rate of 0.2 ml/min. The column was then washed with PBS at 0.5 ml/min until the absorbance at 280 nm (A280 nm) of the column effluent reached baseline. Specifically bound material was eluted with a step gradient, indicated by the arrow, of 100 mM glycine-HCl, pH=2.5, at a flow rate of 0.2 ml/min.

The concept underlying the many facets of this invention is the discovery that c-erbB-2 overexpressing cells shed the c-erbB-2 external domain (gp75) into the body fluids of the host mammal. Examples 1, 4, 5 and 6 outline the evidence that led to this finding. A soluble c-erbB-2 derivative (gp75) was found in the supernatants of stably transformed gp75 expressing cells; the protein was found to have a molecular weight of approximately 75K and to compete with a protein present in NIH3T3$_t$ (c-erbB-2 expressing cells) cell lysate. (Example 1.) Examples 4, 5 and 7 respectively detail the detection of shed antigen, with affinity binding characteristics of the c-erbB-2 external domain, in the sera of nude mice bearing tumors induced by c-erbB-2 transfected NIH3T3 cells (NIH3T3$_t$), in human tumor culture supernates, and in human sera from breast cancer patients. This discovery opened the way for the development of novel methods and compositions for the diagnosis and treatment of neoplastic disease in humans and other mammals.

Assays

There are assays herein provided to detect and quantitate three different entities in the body fluids of mammals, preferably humans, wherein those entities are as follows: gp75 proteins/polypeptides: antibodies to gp75 proteins/polypeptides; and the putative ligand to c-erbB-2. Each of the assays provide important information concerning the disease status of the patient, and are individually useful for screening mammals for neoplastic disease, diagnosing neoplastic disease, monitoring the progress of the disease, and for prognosticating the course of the disease and deciding upon appropriate treatment protocols. However, correlation of the results from one or more of these assays, preferably the test results for all three, provide the best profile on the disease condition of a patient.

For example, a patient may present with a large tumor, but the patient's gp75 level may be relatively low. The lowness of the reading may be due to the patient's generation of antibodies to gp75 proteins/polypeptides and not to the smallness of the tumor.

Another example of how correlating the data provides a broader view of the patient's condition concerns the relationship of the putative ligand to gp75. A patient may present with a high level of circulating gp75 proteins/polypeptides but not have neoplastic disease if the patient is not producing the putative ligand; if there is no ligand, the c-erbB-2 cell surface receptor cannot be stimulated thereby to begin unregulated growth. Thus, the ratio of ligand to gp75 is significant under the model of a ligand/receptor complex being the mechanism by which the proto-oncogene is activated to an oncogene.

Assay for gp75 Proteins/Polypeptides in Mammalian Body Fluids

Non-invasive diagnostic assays are provided to detect gp75 proteins/polypeptides in the body fluids of mammals, preferably humans, and quantitate the level of such gp75 proteins/polypeptides therein. The term gp75 proteins/polypeptides is used in this context as the target antigen in the body fluids, because the shed gp75 protein can be broken down in a patient's body fluids into various fragments, that constitute proteins (having greater than 50 amino acids) and polypeptides (less than 50 amino acids).

Such assays provide valuable means of monitoring the status of neoplastic diseases. In addition to improving prognostication, knowledge of the disease status allows the attending physician to select the most appropriate therapy for the individual patient. For example, patients with a high likelihood of relapse can be treated rigorously, usually involving systemic chemotherapy and/or radiation therapy. When there is a lesser likelihood of relapse, less aggressive therapies can be chosen. Because of the severe patient distress caused by the more aggressive therapy regimens, it would be desirable to distinguish with a high degree of certainty those patients requiring such aggressive therapies.

The present invention is useful for screening a wide variety of neoplastic diseases, including both solid tumors and hemopoietic cancers. Exemplary neoplastic diseases include carcinomas, such as adenocarcinomas and melanomas; mesodermal tumors, such as neuroblastomas and retinoblastomas; sarcomas, such as osteosarcomas, Ewing's sarcoma, and various leukemias; and lymphomas. Of particular interest are tumors of the breast, ovaries, gastrointestinal tract, including the colon and stomach in particular, liver, thyroid glands, prostate gland, brain, pancreas, urinary tract (including bladder), and salivary glands. Of still further particular interest are tumors of the prostate gland, ovaries and breast. Still more specifically, adenocarcinomas of the breast and ovaries have been widely studied and confirmed to overexpress c-erbB-2.

The body fluids that are of particular interest in assaying for gp75 according to the methods of this invention include serum, semen, breast exudate, saliva, urine, cytosols, plasma and cerebrospinal fluid. Serum is a preferred body fluid for screening according to the methods of this invention.

From a knowledge of the structure of the external domain of the c-erbB-2 oncogene (gp75), a number of monoclonal or polyclonal antibodies can be generated that specifically recognize this protein. Because gp75 is uniquely and specifically liberated from the surface of tumors associated with c-erbB-2 amplification and can exist freely in the biological fluids of mammals, it is possible to detect and quantitate the levels of the protein. Utilizing current antibody detection techniques that can quantitate the binding of monoclonal antibodies made specifically to the external domain of the c-erbB-2 oncogene, one can determine the amount of external domain in the fluids of cancer patients. Such an assay can be used to detect tumors, quantitate their growth, and help in the diagnosis and prognosis of the human disease. The assays involve the use of monoclonal or polyclonal antibodies which can be appropriately labeled to detect and quantitate gp75 in body fluids of mammals.

The subject of the invention provides methods and compositions for evaluating the probability of the presence of malignant cells in a group of normal cells in the host or cells freshly removed from the host. A preferred method involves, as a first step, obtaining a purified amount of the external domain of the c-erbB-2 oncogene and using it as an immunogen to generate monoclonal antibodies in mice or other suitable hosts. The monoclonal antibodies should specifically react with epitopes on gp75. Alternatively, whole intact cells expressing c-erbB-2 on their membrane surface could be used as a source of antigen. It is possible that numerous monoclonal antibodies could be generated to recognize different epitopes on the external domain, and these monoclonal antibodies can be used either singularly or in combination as a cocktail to increase the specificity and sensitivity of an assay. Besides using the whole external domain as an immunogen, fragments of this protein, or protein generated by recombinant DNA means, can be also used to generate specific monoclonal antibodies. Also, polypeptides corresponding to various sequences within the external domain sequence could also be used as a source of immunogens. In all cases, the antibodies generated would have a specificity such that they have very limited cross-reactivity with other proteins present on the surface of both tumors and non-tumor cells. They would not, for example, react with the EGF receptor which is present on the surface of many normal cells. The diagnostic assay itself would typically involve obtaining a small amount of body fluid, preferably serum, from the human host. The presence of the c-erbB-2 external domain in the serum can then be quantitated using a number of well-defined antibody diagnostic assays. These can be Western blots, ELISAs (enzyme-lined immunosorbent assays), RIA assays (radioimmunoassay), or dual antibody sandwich assays, all commonly used in the diagnostic industry. In all cases, the interpretation of the results is based on the assumption that the antibody or antibody combination will not cross-react with other protein and protein fragments present in the serum that are unrelated to c-erbB-2. These methods are based on the fact that the presence of the c-erbB-2 external domain bears a strong correlation with the presence of a tumor as outlined above in the Background. The assays can be used to detect the presence of a tumor, detect continued growth of a tumor, and detect the presence of cancer metastasis, as well as confirm the absence or removal of all tumor tissue following surgery, cancer chemotherapy or radiation therapy. It can further be used to monitor cancer chemotherapy and tumor reappearance.

Example 3 details the format of a preferred diagnostic method of this invention—a double sandwich immunoradiometric assay (IRMA). Many other formats for detection of gp75 in body fluids are of course available, including, for example, enzyme linked immunosorbent assays (ELISA). Representative of one type of ELISA test is a format wherein a microtiter plate is coated with antibodies to gp75 proteins/ polypeptides or antibodies to whole cells expressing, preferably overexpressing c-erbB-2 (that is, to intact gp75) and to this is added a sample of patent's serum. After a period of incubation permitting any antigen to bind to the antibodies, the plate is washed and another set of anti-gp75 antibodies which are linked to an enzyme is added, incubated to allow reaction to take place, and the plate is then rewashed. Thereafter, enzyme substrate is added to the microtitre plate and incubated for a period of time to allow the enzyme to work on the substrate, and the absorbance of the final preparation is measured. A large change in absorbance indicates a positive result.

It is also apparent to one skilled in the art of diagnostic assays that antibodies to gp75 proteins and/or polypeptides can be used to detect and quantitate the presence of gp75 in the body fluids of patients. In one such embodiment, a competition immunoassay is used, wherein the gp75 protein/polypeptide is labeled and a body fluid is added to compete the binding of the labeled gp75 to antibodies specific to gp75 protein/polypeptide. Such an assay could be used to detect gp75 protein/polypeptide.

In another embodiment, an immunometric assay may be used wherein a labeled antibody to a gp75 protein or polypeptide is used. In such an assay, the amount of labeled antibody which complexes with the antigen-bound antibody is directly proportional to the amount of gp75 in the body fluid. Monoclonal antibodies for use in the assays of this invention may be obtained by methods well known in the art, particularly the process of Kohler and Milstein reported in *Nature*, 256:495-497 (1975).

Such diagnostic methods can be embodied in test kits to assay for gp75 in mammalian, preferably human, body fluids wherein such test kits can comprise antibodies, polyclonals and/or monoclonals, to gp75 proteins and/or polypeptides, and/or antibodies to whole cells expressing c-erbB-2 (that is, to intact gp75). Such diagnostic test kits can further comprise another set of antibodies, polyclonal and/or monoclonal, for a sandwich format wherein said second set of antibodies are appropriately labeled.

Once antibodies having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting the serum antigen include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098.876.

Antibodies employed in assays may be labeled or unlabeled. Unlabeled antibodies may be employed in agglutination; labeled antibodies may be employed in a wide variety of assays, employing a wide variety of labels.

In some techniques, it will be useful to label the antigen or fragment thereof, rather than the antibody and have a competition between labeled antigen and antigen in the sample for antibody. In this situation, it is common to provide kits which have the combination of the labeled antigen or labeled fragment and the antibody in amounts which provide for optimum sensitivity and accuracy.

In other situations, it is desirable to have a solid support, where either antigen or antibody is bound. A polyepitopic antigen can service as a bridge between antibody bound to a support and labeled antibody in the assay medium. Alternatively, one may have a competition between labeled antigen and any antigen in the sample for a limited amount of antibody.

Suitable detection means include the use of labels such as radionuclides, enzymes, fluorescers, chemiluminescers, enzyme substrates or co-factors, enzyme inhibitors, particles, dyes and the like. Such labeled reagents may be used in a variety of well known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

Assays for Antibodies to gp75
Proteins/Polypeptides

As indicated above, the level of antibodies to gp75 proteins/polypeptides in a patient's body fluids is an important parameter in screening for neoplastic disease, monitoring, and prognosticating the course of the disease and on deciding on a course of treatment. A representative assay to detect such antibodies is a competition assay in which labeled gp75 protein/polypeptide is precipitated by antibodies in patient serum in combination with monoclonal antibodies recognizing gp75 protein/polypeptides. One skilled in the art could adapt any of the formats outlined and referred to in the above section to detect anti-gp75 antibodies for the quantitation of antibodies to gp75.

Assays for Putative Ligand to C-erbB-2

Similarly useful for diagnosing and screening for neoplastic disease and monitoring and prognosticating the course of the disease and treatment schedules, is an assay to detect and quantitate the level of the putative ligand to the c-erbB-2 receptor. Such an assay would be especially useful in correlation with one of the above assays for gp75 proteins/polypeptides and antibodies thereto, and more preferably in correlation with both such assays.

A representative format for such an assay for the c-erbB-2 ligand utilizing gp75 proteins/polypeptides would involve attaching purified, preferably substantially pure, gp75 proteins/polypeptides to a plastic surface or other solid support either by its own binding to such surface or via a capture anti-gp75 antibody. Utilizing a competition assay of labeled ligand with an unknown amount of unlabeled ligand, the concentration of the latter for binding to the gp75 proteins/polypeptides can be quantitated utilizing standard diagnostic instrumentation.

Alternative formats, labeling, and in general other modifications which are within the scope of knowledge of those skilled in the art as outlined above for assays for gp75 proteins/polypeptides, similarly apply to the assays to detect and quantitate the putative ligand to c-erbB-2.

Anti-Idiotype Antibodies to Antibodies to gp75
Proteins/Polypeptides

Further within the scope of this invention are anti-idiotype antibodies to antibodies to gp75 proteins/polypeptides. In each instance in the above-outlined assays, such anti-idiotype antibodies can substitute for gp75 proteins/polypeptides.

Still further as noted under Vaccines, such anti-idiotype antibodies can be used as immunogenic agents.

Anti-idiotype antibodies to anti-gp75 antibodies are prepared essentially as outlined above in the Methods section: Preparation of Monoclonal c-erbB-2 Antibodies wherein the initial immunization is with the appropriate anti-gp75 antibody rather than the NIH3T3$_t$ cells. The fusion protocol is similarly followed therein. The screening process is a primary screen for binding to the original anti-gp75 monoclonal used for immunization, and a secondary screen comprising a competition assay, for example, a radiometric assay, wherein the appropriate gp75 protein/polypeptide competes with the anti-idiotype antibodies produced in the fusion for binding with the radiolabeled original anti-gp75 monoclonal.

Test Kits

The above outlined assays can be embodied in the form of test kits. Said test kits can comprise antibodies to gp75 proteins/polypeptides and/or antibodies to the intact gp75 (that is, on the surface of cells expressing c-erbB-2). Said antibodies can be either polyclonal and/or monoclonal. Further said test kits can comprise gp75 proteins/polypeptides alone or in combination with the aforementioned antibodies. As indicated above, anti-idiotype antibodies to anti-gp75 antibodies can be substituted for appropriate gp75 proteins/polypeptides in such test kits.

Exemplary would be a test kit to assay for the putative ligand wherein either gp75 protein/polypeptides are coated on a surface or captured thereon or anti-idiotype antibodies to anti-gp75 antibodies are so coated on a surface. Alternatively, such an assay can be formulated as a competition assay as outlined above. Of course, such assays are not limited to solid phase assays, but can be in a liquid phase format and can be based on enzyme-limited immunosorbent assay (ELISAs) particle assays, radiometric or fluormetric assays, either unamplified or amplified using, for example avidin/biotin technology.

Preparation of gp75 Proteins and Polypeptides

The gp75 proteins and polypeptides of this invention, can be prepared in a variety of ways. A preferred method to prepare gp75 proteins is by recombinant means. A representative recombinant method of this invention is described infra in Example 1.

The gp75 proteins and polypeptides of this invention can further be prepared synthetically or biologically, that is, by cleaving longer proteins and polypeptides enzymatically and/or chemically. Said synthetic and biologic methods are described in detail infra under the heading Synthetic and Biologic Production of gp75 Protein and Polypeptide Portions Thereof. Such methods are preferred for preparing gp75 polypeptides.

Cloning of gp75 Sequence or Fragments Thereof

The plasmid pFRSV-c-erbB-2sec, constructed in accordance with Example 1, is only representational of the many possible DNA recombinant molecules that can be prepared in accordance with this invention. Depending on the restriction endonucleases employed, all or part of the c-erbB-2 external domain sequence may be cloned, expressed and used in accordance with this invention.

Useful restriction enzymes according to this invention may include enzymes that cleave DNA in such a way that the DNA fragment generated contains portions of the gp75 sequence. Appropriate restriction endonucleases may be selected by those of skill in the art on due consideration of the factors set out herein without departing from the scope of the invention.

A representative cloning vehicle used in Example 1 is pSV7186. However, a wide variety of host-cloning vehicle combinations may be usefully employed in cloning the gp75 DNA. For example, useful cloning vehicles may include chromosomal, nonchromosomal and synthetic DNA sequences such as various known bacterial plasmids such as pBR322, other *E. coli* plasmids and their derivatives and wider host range plasmids such as RP4, phage DNA such as the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic, preferably eukaryotic, and include bacterial hosts such as *E. coli* strains CAG456, JM103, N4830, X1776, X2282, HB101 and MRC1 and strains of *Pseudomonas, Bacillus subtilis* and other bacilli, yeasts and other fungi, animal or plant hosts such as animal or plant cells in culture, insect cells and other hosts. Preferred hosts in accordance with this invention are yeast cells, mammalian cells in culture, preferably monkey cells and Chinese Hamster Ovary (CHO) cells. Preferable monkey cells are from the cell line COS7; preferable CHO cells are from the cell line CHO-(dxb11). Of course, not all hosts may be equally efficient. The particular selection of host-cloning vehicle combination may be made by those of skill in the art after due consideration of the principles set forth herein without departing from the scope of this invention.

Furthermore, within each specific vector, various sites may be selected for insertion of the isolated double-stranded DNA. These sites are usually designated by the restriction enzyme or endonuclease that cuts them. For example, in pBR322 the PstI site is located in the gene for penicillinase between the nucleotide triplets that code for amino acids 181 and 182 of the penicillinase protein.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art. None of these factors alone absolutely controls the choice of insertion site for a particular protein or polypeptide, but rather the site chosen effects a balance of these factors and not all sites may be equally effective for a given protein.

It should, of course, be understood that the nucleotide sequence or gene fragment inserted at the selected restriction site of the cloning vehicle may include nucleotides which are not part of the actual structural gene for the desired protein or may include only a fragment of that structural gene. It is only required that whatever DNA sequence is inserted, the transformed host will produce a protein or polypeptide displaying epitopes of gp75.

The recombinant DNA molecule containing the hybrid gene may be employed to transform a host so as to permit that host (transformant) to express the structural gene or fragment thereof and to produce the protein or polypeptide for which the hybrid DNA codes. The recombinant DNA molecule may also be employed to transform a host so as to permit that host on replication to produce additional recombinant DNA molecules as a source of gp75 DNA and fragments thereof. The selection of an appropriate host for either of these uses is controlled by a number of factors recognized by the art. These include, for example, compatibility with the chosen vector, toxicity of the co-products, ease of recovery of the desired protein or polypeptide, expression characteristics, biosafety and costs. No absolute choice of host may be made for a particular recombinant DNA molecule or protein or polypeptide from any of these factors alone. Instead, a balance of these factors may be struck with the realization that not all hosts may be equally effective for expression of a particular recombinant DNA molecule.

Expression of gp75 Proteins/Polypeptides

Where the host cell is a procaryote such as *E. coli*, competent cells which are capable of DNA uptake are prepared from cells harvested after exponential growth phase and subsequently treated by the calcium chloride ($CaCl_2$) method by well known procedures. Transformation can also be performed after forming a protoplast of the host cell.

Where the host used is an eucaryote, transfection method of DNA as calcium phosphate-precipitate, conventional mechanical procedures such as microinjection, insertion of a plasmid encapsulated in red blood cell hosts or in liposomes, treatment of cells with agents such as lysophosphatidyl-choline or use of virus vectors, or the like may be used.

The level of production of a protein or polypeptide is governed by two major factors: the number of copies of its gene or DNA sequence encoding for it within the cell and the efficiency with which these gene and sequence copies are transcribed and translated. Efficiencies of transcription and translation (which together comprise expression) are in turn dependent upon nucleotide sequences, normally situated ahead of the desired coding sequence.

These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), a fusion of the trp and lac promoter ("the tac system"), the major operator and promoter regions of phage λ ($O_L P_L$ and $O_R P_R$,), and the control region of the phage fd coat protein. DNA fragments containing these sequences are excised by cleavage with restriction enzymes from the DNA isolated from transducing phages that carry the lac or trp operons, or from the DNA of phage λ or fd. These fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation of the appropriate hosts and the level of antigen production is measured. Cells giving the most efficient expression may be thus selected. Alternatively, cloning vehicles carrying the lac, trp or λ $P_L$ control system attached to an initiation codon may be employed and fused to a fragment containing a sequence coding for a gp75 protein or polypeptide such that the gene or sequence is correctly translated from the initiation codon of the cloning vehicle.

Synthetic and Biologic Production of gp75 Protein and Polypeptide Fragments Thereof gp75 proteins and polypeptides of this invention may be formed not only by recombinant means but also by synthetic and by other biologic means. Exemplary of other biologic means to prepare the desired polypeptide or protein is to subject to selective proteolysis a longer gp75 polypeptide or protein containing the desired amino acid sequence; for example, the longer polypeptide or protein can be split with chemical reagents or with enzymes. Synthetic formation of the polypeptide or protein requires chemically synthesizing the desired chain of amino acids by methods well known in the art.

The portion of a longer polypeptide or protein which contains the desired amino acids sequence can be excised by any of the following procedures:

(a) Digestion of the protein or longer polypeptide by proteolytic enzymes, specially those enzymes whose substrate specifically results in cleavage of the protein or polypeptide at sites immediately adjacent to the desired sequence of amino acids.

(b) Cleavage of the protein or polypeptide by chemical means. Particular bonds between amino acids can be cleaved by reaction with specific reagents. Examples include: bonds involving methionine are cleaved by cyanogen bromide; asparaginyl glycine bonds are cleaved by hydroxylamine; disulfide bonds between two cysteine residues are cleaved by reduction, e.g., with dithiothreitol.

(c) A combination of proteolytic and chemical changes. Of course, as indicated above, it should also be possible to clone a small portion of the DNA that codes for the synthetic peptide, resulting in the production of the peptide by the unicellular host.

The biologically or synthetically produced proteins and polypeptides once produced, may be purified by gel filtration, ion exchange or high pressure liquid chromatography, or other suitable means.

Chemical synthesis of polypeptides is described in the following publications: Merrifield et al., *J. Am. Chem. Soc.*, 85:2149-2156 (1963); Kent et al., *Synthetic Peptides in Biology and Medicine,* 29 ff., eds Alitalo et al. (Elsevier Science Publishers 1985); Haug, *ABL,* 40-47 (January/February 1987); Andrews, *Nature,* 319:429-430 (Jan. 30, 1986); Kent, *Biomedical Polymers,* 213-242, eds. Goldberg et al. (Academic Press 1980); Mitchell et al., *J. Org. Chem.*, 43: 2845:2852 (1978); Tam et al., *Tet. Letters,* 4033-4036 (1979); Mojsov et al., *J. Org. Chem.*, 45: 555-560 (1980); Tam et al. *Tet Letters,* 2851-2854 (1981); and Kent et al., *Proceedings of the IV International Symposium on Methods of Protein Sequence Analysis* (Brookhaven Press 1981).

The "Merrifield solid phase procedure" as described in the above-mentioned publications can be used to build up the appropriate sequence of L-amino acids from the carboxyl terminal amino acid to the amino terminal amino acids. Starting with the appropriate carboxyl terminal amino acid attached to an appropriate resin via chemical linkage to a chloromethyl group, benzhydrylamine group, or other reactive group of the resin, amino acids are added one by one using the following procedure for each:

(a) Peptidyl resin is washed with methylene chloride;

(b) the resin is neutralized by mixing for 10 minutes at room temperature with 5% (v/v) diisoproplethylamine (or other hindered base) in methylene chloride;

(c) the resin is washed with methylene chloride;
(d) an amount of amino acid equal to six times the molar amount of the growing peptide chain is activated by combining it with one-half as many moles of a carbodiimide, e.g. dicyclohexylcarbodiimide, diisopropylcarbodiimide, for 10 minutes at 0° C., to form the symmetric anhydride of the amino acid. The amino acid used should be provided originally as the N-α-butyloxycarbonyl derivative, with side chains protected with benzyl ester (aspartic and glutamic acids), benzyl ethers (serine, threonine, cysteine, tyrosine), benzyl oxycarbonyl groups (lysine) or other protecting groups commonly used in peptide synthesis;
(e) the activated amino acid is reacted with the peptidyl resin for 2 hours at room temperature resulting in addition of the new amino acid to the end of the growing peptide chain;
(f) the resin is washed with methylene chloride;
(g) The N-α-(butyloxycarbonyl) group is removed from the most recently added amino acid by reacting with 30% (v/v) trifluoracetic acid in methylene chloride for 30 minutes at room temperature;
(h) the resin is washed with methylene chloride;
(i) steps a through h are repeated until the required peptide sequence has been constructed. The peptide is then removed from the resin and simultaneously the side-chain protecting groups are removed, by reacting with anhydrous hydrofluoric acid containing 10% (v/v) of anisole. Subsequently, the peptide can be purified by gel filtration, ion exchange, or high pressure liquid chromatography, or other suitable means.

Chemical synthesis can be carried out without a solid phase resin, in which case the synthetic reactions are performed entirely in solution. The reactions, and the final product, are otherwise essentially identical.

Techniques of chemical peptide synthesis include using automatic peptide synthesizers, employing commercially available protected amino acids; such synthesizers include, for example, Biosearch (San Rafael, Calif.) Models 9500 and 9600, Applied Biosystems Inc. (Foster City, Calif.) Model 430, and MilliGen (a division of Millipore Corp.) Model 9050. Further, one can manually synthesize up to about 25 polypeptides at a time by using Dupont's Ramp (Rapid Automated Multiple Peptide Synthesis).

The synthetic polypeptides according to this invention preferably comprise one or more epitopes of the gp75. It is possible to synthesize such polypeptides by attaching the amino acid sequence which defines an epitope (which can be from about three to about eleven amino acids, more usually from about five to about eleven amino acids) to at least three amino acids flanking either side thereof. The three amino acids on either side can be the same amino acids as in the natural gp75 sequence or could be other amino acids.

Antibodies to gp75

Antibodies to the recombinant, synthetic or natural gp75 proteins and polypeptides, of this invention, have use not only for diagnostic assays but also for affinity purification of gp75 proteins/polypeptides and for therapeutic use. As indicated above in the Background, antibodies to c-erbB-2 have been shown to inhibit tumor growth in vitro and in vivo [Drebin et al., supra (1985)].

Vaccines

It will be readily appreciated that the gp75 proteins and polypeptides of this invention can be incorporated into vaccines capable of inducing protective immunity against neoplastic disease and a dampening effect upon tumorigenic activity. Polypeptides may be synthesized or prepared recombinantly or otherwise biologically, to comprise one or more amino acid sequences corresponding to one or more epitopes of the gp75 either in monomeric or multimeric form. These polypeptides may then be incorporated into vaccines capable of inducing protective immunity against gp75. Techniques for enhancing the antigenicity of such polypeptides include incorporation into a multimeric structure, binding to a highly immunogenic protein carrier, for example, keyhole limpet hemocyanin (KLH), or diphtheria toxoid, and administration in combination with adjuvants or any other enhancers of immune response.

It will further be appreciated that anti-idiotype antibodies to antibodies to gp75 proteins/polypeptides are also useful as vaccines and can be similarly formulated.

An amino acid sequence corresponding to an epitope of gp75 either in monomeric or multimeric form may be obtained by chemical synthetic means or by purification from biological sources including genetically modified microorganisms or their culture media. [See Lerner, "Synthetic Vaccines", Sci. Am. 248(2):66-74 (1983).] The polypeptide may be combined in an amino acid sequence with other polypeptides including fragments of other proteins, as for example, when synthesized as a fusion protein, or linked to other antigenic or non-antigenic polypeptides of synthetic or biological origin.

The term "corresponding to an epitope of a gp75" will be understood to include the practical possibility that, in some instances, amino acid sequence variations of naturally occurring protein and polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring gp75 proteins and polypeptides to a sufficient extent to provide protective immunity and/or anti-tumorigenic activity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the gp75 proteins or polypeptides, preferably in quantities providing unit doses of from 0.01 to 10.0 micrograms of immunologically active gp75 protein and/or polypeptide per kilogram of the recipient's body weight. Total protective doses may range from 0.1 to about 100 micrograms of antigen.

Routes of administration, antigen dose, number and frequency of injections are all matters of optimization within the scope of ordinary skill in the art.

Therapeutic Use of gp75 Proteins and Polypeptides

The gp75 proteins and polypeptides of this invention may further be used therapeutically in the treatment of neoplastic disease, either alone or in combination with chemotherapeutic drugs. The fact that the external domain of c-erbB-2 is shed into body fluids as an intact molecule lends itself to therapeutic uses. An excess of gp75 unattached to the cell may compete with and interfere with the binding of the putative ligand for c-erbB-2 to the oncogene's cell surface receptor in a manner analogous to that of the CD4 receptor and HIV-1's gp120 envelope protein as outlined above in the Background [Smith et al., supra, (1987)]. Alternative mechanisms to explain the therapeutic effects of gp75 proteins and polypeptides may be to prevent or disrupt receptor/receptor interaction between c-erbB-2 expressing cells that facilitate tumorigenicity.

Such therapeutic methods comprise the administration of c-erbB-2 external domain material, its fragments, or peptides derived from part of its sequence, to patients. The high circulating levels of gp75 proteins/polypeptides could be expected to reduce or eliminate tumor growth as described above. The gp75 protein/polypeptides can be administered in a therapeutically effective amount dispersed in a physiologically acceptable, nontoxic liquid vehicle. Routes of administration and dosages may be similar to those noted under Vaccines above.

Definitions

The term "gp75" is herein defined to mean a glycoprotein having an approximate molecular weight of 75 kilodaltons (kd) that constitutes the external domain of the approximately 185 kd glycoprotein (gp185) that is c-erbB-2. The term "gp75" is precisely defined by its nucleotide and amino acid sequences shown in FIG. 16; the gp75 external domain comprises the region from about amino acid number 22 (serine; ser-22) to about amino acid number 653 (serine: ser-653) (said amino acids are marked by black circles above them in FIG. 16) with the nucleotide sequence corresponding thereto. The amino acid sequence represents the nonglycosylated version of gp75 which would be expected to have an approximate molecular weight of 69 kd (Coussens et al., supra). Included within the scope of the term gp75 are glycoproteins produced recombinantly by yeast and higher eukaryotes that have varying amounts of glycosylation which affect the molecular weight of the protein product: for example, a small amount of gp90 was produced in stably transformed gp75-expressing CHO cells as indicated in Example 1 below.

The phrase "intact gp75" is herein defined to mean the gp75 external domain expressed upon the surface of a cell. Therefore, the intact gp75 would still be attached to the cell through the transmembrane region.

A "polypeptide" is a chain of amino acids covalently bound by peptide linkages and is herein considered to be composed of 50 or less amino acids. A "protein" is herein defined to be a polypeptide composed of more than 50 amino acids.

The phrase "gp75 proteins and polypeptides" is herein defined to mean proteins and polypeptides which are encoded by the gp75 external domain DNA sequence as shown in FIG. 16 (nucleotides encoding from approximately ser-22 to approximately ser-653) or by fragments of said gp75 DNA sequence. The phrase "gp75 proteins and polypeptides" is herein interpreted to include proteins and polypeptides which have substantially the same amino acid sequences and substantially the same biological activity as the "gp75 proteins and polypeptides".

It is understood that because of the degeneracy of the genetic code, that is, that more than one codon will code for one amino acid [for example the codons TTA, TTG, CTT, CTC, CTA and CTG each code for the amino acid leucine (L)], that variations of the nucleotide sequence of FIG. 16, wherein one codon is substituted for another, would produce a substantially equivalent protein or polypeptide according to this invention. All such variations in the nucleotide sequence for gp75 are included within the scope of this invention.

It is further understood that the gp75 DNA sequence as shown in FIG. 16 represents only the precise structure of the naturally occurring nucleotide sequence. It is expected that slightly modified nucleotide sequences will be found or can be modified by techniques known in the art to code for similarly serologically active, immunogenic and/or antigenic proteins and polypeptides, and such nucleotide sequences and proteins/polypeptides are considered to be equivalents for the purpose of this invention. DNA having equivalent codons is considered within the scope of the invention, as are synthetic DNA sequences that encode proteins/polypeptides homologous or substantially homologous to the gp75 DNA sequence and as are DNA sequences that hybridize to the sequences coding for gp75 proteins/polypeptides, as well as those sequences but for the degeneracy of the genetic code would hybridize to said gp75 sequences. Further, DNA sequences which are complementary to the gp75 sequences referred to herein are within the scope of this invention. Such modifications and variations of DNA sequences as indicated herein are considered to result in sequences that are substantially the same as the gp75 sequence or portions thereof. Typically, such related nucleotide sequences are substantially the same which fall into the definition of substantially homologous.

Further, it will be appreciated that the amino acid sequence of gp75 can be modified by genetic techniques. One or more amino acids can be deleted or substituted. Such amino acid changes, especially if in a region which is not within an epitope of the polypeptide, may not cause any measurable change in the serological, antigenic and/or immunogenic activity of the protein or polypeptide. The resulting protein or polypeptide will have substantially the same amino acid sequence and substantially the same biological activity and is within the scope of the invention.

Preferably, when the gp75 protein/polypeptides are administered with chemotherapeutic agents, those agents are alkylating agents. Preferred chemotherapeutic drugs for the method are cisplatin, carboplatin and mephalan.

| Abbreviations | |
|---|---|
| The following abbreviations are used in this application: | |
| ATCC | American Tissue Culture Collection |
| BCA | bicinchoninic acid |
| BSA | Bovine serum albumin |
| CHO | Chinese hamster ovary |
| DAB | diaminobenzidine tetrahydrochloride |
| DHFR | dihydrofolate reductase |
| DMEM | Dulbecco modified Eagle medium |
| EDTA | ethylenediaminetetraacetic acid |
| EGF | epidermal growth factor |
| EGFr | epidermal growth factor receptor |
| EGTA | ethylene glycol-bis (β-aminoethyl ether)-N,N,N',N' tetraacetic acid |
| ELISA | enzyme labeled immunosorbent assay |
| FACS | fluorescent activated cell sorting |
| FBS | fetal bovine serum |
| FITC | fluorescein isothiocyanate |
| HAT | hypoxanthine aminopterin thymidine |
| HBSS | Hank's balanced salt solution |
| HEPES | 4-(2-hydroxyethyl)-1-piperazineethanesulfonic acid |
| HPLC | high pressure liquid chromatograph |
| HRP | horseradish peroxidase |
| IRMA | immunoradiometric assay |
| MEM | minimal essential medium |
| MTT | 3-(4,5-dimethylthiazoyl-2-yl)-2,5-diphenyl tetrazolium bromide |
| MTX | methotrexate |
| NHS | N-hydroxysuccinimide |
| PBS | phosphate-buffered saline |

Abbreviations
The following abbreviations are used in this application:

| | |
|---|---|
| PEG | polyethylene glycol |
| PMSF | phenylmethylsulfonylfluoride |
| PNPP | para-nitrophenyl phosphate |
| RIA | radioimmunoassay |
| RPMI | Roswell Park Memorial Institute 1640 media |
| RT | room temperature |
| SDS | sodium dodecyl sulfate |
| SDS-PAGE | sodium dodecyl sulfate-polyacrylamide gel electrophoresis |
| TAb/MAb | monoclonal antibody |
| TCA | trichloroacetic acid |
| TMB | tetramethyl benzidine |
| TRIS | tris(hydroxymethyl)aminomethane or amino-2-hydroxymethyl-1,3-propanediol |

Cell Lines
The following cell lines were used in the experiments herein described:

| | |
|---|---|
| SKBR3 | Human breast cancer cell line which originated as a metastatic pleural effusion was obtained from the ATCC, catalog # HTB30. |
| SKOV3 | Human ovarian cancer cell line which originated as a metastatic ascitic effusion was obtained from the ATCC, catalog # HTB77. |
| MCF7 | Human breast adenocarcinoma cell line from a pleural effusion was obtained form the ATCC, catalog # HTB22. |
| MDA361 | Human breast cancer cell line which originated as a metastatic tumor to the brain was obtained from the ATCC, catalog # HTB27. |
| MDA435 | Human breast cancer cell line which originated as a metastatic pleural effusion and is obtainable from the ATCC, catalog # HTB129 |
| MDA468 | Breast cancer cell line which originated as a metastatic pleural effusion and contains amplified EGFr was obtained from the ATCC, catalog # HTB132. |
| NIH3T3 | Murine fibroblast cell line obtained from S. Aaronson (NIH) [Science, 237:178 (1987)] |
| NIH3T3$_t$ | Murine fibroblast cell line transfected with the c-erbB-2 oncogene was obtained from S. Aaronson (NIH) [Science, 237:178 (1987)]. |
| HBL100 | This relatively normal breast cancer cell line derived from human milk is immortalized with SV-40 and was obtained from the ATCC, catalog # HTB124. |
| COS7 | SV40 transformed African green monkey cells were obtained from the ATCC catalog # CRL1651. |
| CHO-(dxb11) | Chinese hamster ovary cells were obtained from the UCSF cell culture facility. |

Growth Media
The following growth media were used, for the cell lines as indicated, in the experiments herein described:

| | |
|---|---|
| SKBR3, MDA468 MDA435 | Cells were cultured in Minimal Essential Medium (MEM), [Gibco Biologicals Inc., New York], 10% heat inactivated fetal bovine serum, 0.29 mg/ml L-glutamine. |
| SKOV3 | Cells were cultured in Iscove's Modified Dulbecco's Medium (IMDM), 10% heat inactivated fetal bovine serum, 0.29 mg/ml L-glutamine. |
| MDA361 | Cells were cultured In RPMI 1640, 10% heat inactivated fetal bovine serum, 1 µg/ml bovine pancreatic insulin, 0.29 mg/ml L-glutamine. |
| HBL100 | Cells were cultured in McCoy's 5A medium, 10% heat inactivated fetal bovine serum, 0.29 mg/ml L-glutamine. |
| COS7 | Cells were routinely maintained in Dulbecco modified Eagle medium (DMEM) supplemented with 10% fetal bovine serum (Gibco Laboratories), 100 µM L-glutamine, 100 units/ml penicillin and 100 µg/ml streptomycin. |
| CHO-(dxb11) | Cells were maintained in α-MEM supplemented with 10% FBS L-glutamine and antibiotics. |
| NIH3T3 NIH3T3$_t$ MCF7 | Cells were maintained in DMEM + 4% FBS, 2 mM glutamine |

REFERENCES

The following are citations for references referred to in the text by author(s) or editor(s) and year designations:

Ausutel et al., (eds.), *Current Protocols in Mol. Biol., Vol. 2*, (Wiley Interscience 1988)
Coussens et al., *Science,* 230:1132 (1985)
Di Fiore et al., *Science,* 237:178 (1987)
Graham and van der Eb (eds.), *J. Virol.* 52:456 (1973)
Horan-Hand et al., *Cancer Res.,* 43: 728 (1983)
Horwich et al., *J. Cell Biol.,* 100: 1515 (1985)
Hsu et al., *J. Histochem.,* 29:577 (1981)
King et al., *Science,* 229:974 (1985)
Laemmli, *Nature,* 227:680 (1970)
Maniatis et al., *Molecular Cloning: A Laboratory Manual,* (Cold Spr. Harbor Lab. 1982)
McConglogue, *Gene Transfer Vectors for Mammalian Cells,* pp 79-84 (CSH Publishing 1987)
Slamon et al., "Studies of the HER-2/neu proto-oncogene in human breast cancer". *Cancer Cell 7/Molecular Diagnostics of Human Cancer,* pp. 371-384, (CSH, NY 1989)
Towbin et al., *PNAS,* 76:4350 (1979)
Zoller and Smith, *Methods Enzymol.* 154: 329 (1987).

Methods

The following methods were used in the examples below.

Protein Analysis

Proteins were analyzed by SDS-PAGE as described by Laemmli, *Nature,* 227:680-685 (1970), which article is herein incorporated by reference, using a 4% acrylamide stacking gel with a 10% resolving gel, both containing 0.2% SDS. Samples were applied in 50 microliter (µl) of sample buffer [63 millimolar (mM) TRIS, pH 6.8, 10% glycerol, 5% 2-mercaptoethanol, and 2.3% SDS] and were electrophoresed for four hours with a constant current of 20 milliampere (mA). The molecular weights of proteins were estimated by their mobilities relative to standard proteins of known molecular weight. Protein concentration was determined using a Coomassie blue dye-binding assay (Bio-Rad Laboratories, Richmond, Calif.).

Western Blots

To characterize an antigen identified by an appropriate antibody, a modification of the Western blot as described by Towbin et al., *Proc. Natl. Acad. Sci., U.S.A.,* 76:4350-4354 (1979), which article is herein incorporated by reference, was used in which the proteins are transferred from SDS-PAGE gels to nitrocellulose filters and identified by the appropriate monoclonal antibody. After transfer to the nitrocellulose filters, excess protein binding sites were blocked by soaking the filters in PBS containing 3% BSA. The antigen was located by incubating the sheet in 30 milliliter (ml) of PBS containing 1% BSA and 1-2×10$^7$ counts per minute (cpm) of iodinated antibody for one hour. The filter was then rinsed, dried, and autoradiographed. (As little as 100 picogram (pg) of protein can be detected with this procedure.)

Preparation of Antibodies

Preparation of Polyclonal Antibody: 92

New Zealand white rabbits were immunized with 50-200 μg E. coli recombinant antigen representing the N-terminal 81% of the c-erbB-2 protein. The initial immunization consisted of the antigen emulsified 1:1 (vol/vol) in Freund's complete antigen, and injected at two subcutaneous sites. Two subsequent boosts were given at two week intervals, with the antigen emulsified in incomplete adjuvant. The animals were bled every two weeks via ear vein and the sera assayed by Western blot against gp185 expressing cell lysates, by reactivity on the cell based ELISA (described below), by immunoprecipitation of the gp185 protein from radiolabeled cell lysates, and by immunoprecipitation of the gp170 protein from radiolabeled A431 cell lysates. The sera demonstrated strong reactivity with gp185 by Western blot after 2 boosts and cross-reacted with the EGF receptor protein.

Preparation of Polyclonal Antibody: 9.2

Rabbit polyclonal antiserum was made against a 14 amino acid peptide at the C-terminus of the c-erbB-2 protein. An immunization similar to that described above was used. This antiserum specifically precipitates a 185 kd protein from membrane preparations of cells expressing the c-erbB-2 protein. It does not cross-react with the EGF receptor.

Preparation of Monoclonal c-erbB-2 Antibodies

Balb/c mice were immunized intraperitoneally and subcutaneously with either 2×10$^6$-1×10$^7$ NIH3T3 cells transfected with the c-erbB-2 oncogene, NIH3T3$_t$, (kindly provided by Dr. S. Aaronson, NIH) [Di Fiore et al., *Science*, 237:178-182 (1987)], or with a similar number of SKBR3 cells emulsified 1:1 (vol/vol) in complete Freund's adjuvant. The animals were boosted every two to four weeks with cells emulsified in incomplete adjuvant. Sera was collected every two weeks and tested for reactivity in an ELISA assay (described below) against formalin fixed NIH3T3 or fixed NIH3T3$_t$ cells. Animals with positive titers were boosted intraperitoneally or intravenously with cells in PBS, and animals were sacrificed 4 days later for fusion. Spleen cells were fused with P3-X63Ag8.653 myeloma cells at a ratio of 1:1 to 7.5:1 with PEG 4000 as described by the procedure of Kohler and Milstein [*Nature*, 256:495-497 (1975)]. Fused cells were gently washed and plated in 96-well plates at 1-4×10$^6$ cells/ml in RPMI. Wells were fed with HAT medium 24 hours after the fusion and then every 3 days for 2-3 weeks. When colony formation was visible, after 10-14 days, the supernatants were tested for reactivity in the ELISA assay. Prospective clones demonstrating good growth were expanded into 24-well plates and rescreened 7-10 days later. Positive wells were then assayed for external domain reactivity against live NIH3T3 and NIH3T3$_t$ cells by flow sorting analysis. Hybridomas (designated parent hybridomas) which were positive both by ELISA assay and flow sorting analysis were cloned either by limiting dilution cloning or by single cell deposition, based on flow sorting analysis of surface immunoglobulin expression, into 96-well plates containing spleen feeder cells. Wells demonstrating growth were retested by ELISA and recloned an additional one to three times. Supernatants from hybridoma clones were tested for isotype and subisotype, reactivity to surface expressed gp185 protein on NIH3T3$_t$ cells by flow sorting analysis, and immunoprecipitation of a labeled gp185 protein from transfected cells. Positive hybridomas were grown and injected into pristane-primed Balb/c mice, Balb/c nude mice or IRCF$_1$ mice for ascites production. Ascites were purified by HPLC on a Bakerbond ABx column and purified monoclonal antibodies (referred to by TAb #) were dialyzed against PBS and stored at −20° C. All purified antibodies were tested for isotype and subisotype by radial immunodiffusion (with less than 15% contaminating isotypes) cell surface staining of gp185 expressing cell lines by flow sorting analysis, ELISA assay against transfected and untransfected NIH3T3 cells, radioimmunoprecipitation of gp185 from labeled c-erbB-2 expressing cell lines, lack of cross-reactivity with the closely related EGF-receptor protein by the failure to precipitate a radiolabeled 170 kD protein from radiolabeled A-431 cells, and analyzed by SDS-PAGE and gel densitometry (all purified proteins are >90% immunoglobulin). All monoclonal antibodies failed to recognize the gp185 protein by Western blot techniques. A summary of the MAbs developed to date and the reactivity of these MAbs is outlined in Table 1. A29 is the parent hybridoma to monoclonal antibodies, TAB 250-254. In some of the early experiments, as indicated, the supernatant from the A29 hybridoma was used.

TABLE 1

Reactivity of MAbs Recognizing the External Domain of c-erbB-2

| TAb | Immunoqen | Clone Designation | FACS[1] Binding | ELISA[2] Titer, ng/ml | Subisotype | RIP gp185 | gp170 | gp75 | Western Blot |
|---|---|---|---|---|---|---|---|---|---|
| 250 | NIH3T3$_t$ | 189A29-1 | + | 20 | IgG$_1$ | + | − | + | − |
| 251 | " | 189A29-5 | + | 1 | " | + | − | + | − |
| 252 | " | 189A29-1C | + | 20 | " | + | − | + | − |
| 253 | " | 189A29-1B | + | 47 | " | + | − | + | − |
| 254 | " | 189A29-4-52 | + | 10 | " | + | − | + | − |
| 255 | " | 298E95-31-3 | + | 16 | " | + | − | +/− | − |
| 256 | " | 296A60-34-7 | + | 25 | " | + | − | + | − |
| 257 | " | 296Ag4-74-28 | + | 11 | " | + | − | + | − |
| 258 | " | 297E10-23-17 | + | 4 | " | + | − | + | − |
| 259 | SKBR3 | 292D12B-93-61 | + | 20 | " | + | − | + | − |
| 260 | NIH3T3$_t$ | 272D69C-85-40 | + | 10 | IgG$_{2a}$ | + | − | + | − |
| 261 | " | 297D12-80-32 | + | 10 | IgG$_{2b}$ | + | − | +/− | − |
| 262 | " | 297C65-43-71 | + | 27 | IgG$_1$ | + | − | + | − |
| 263 | " | 297D11-34-14 | + | 100 | IgG$_{2b}$ | + | − | + | − |

TABLE 1-continued

Reactivity of MAbs Recognizing the External Domain of c-erbB-2

| TAb | Immunoqen | Clone Designation | FACS[1] Binding | ELISA[2] Titer, ng/ml | Subisotype | RIP gp185 | gp170 | gp75 | Western Blot |
|---|---|---|---|---|---|---|---|---|---|
| 264 | " | 297E87-8-95 | + | 41 | IgG$_1$ | + | − | + | − |
| 265 | " | 298D57-8-36 | + | 51 | IgG$_1$ | + | − | + | − |

[1]Ability to bind to NIH3T3 cells transfected with c-erbB-2 with a mean peak fluorescence at least 2× over background binding to untransfected NIH3T3 cells
[2]Titer at 30% maximum binding in an ELISA assay against NIH3T3 cells transfected with c-erbB-2.

Flow Sorting Analysis

NIH3T3 and NIH3T3$_t$ (or other c-erbB-2 expressing cell line) cells were grown to 80% confluency in DMEM+4% FBS. Cells were harvested with Puck's Versene, and washed twice with cold FACS buffer (HBSS without phenol red, 2% FBS, 0.2% sodium azide, 10 mM HEPES). Cells were distributed at 0.5-1.0×10$^6$ cells per 12×75 mm glass test tube (cells should be >90% viable), pelleted, and the supernatants removed. The tubes were placed on ice and 100 µl of supernatants or purified antibodies were added per tube. Each antibody or supernatant was tested against both NIH3T3 cells as well as NIH3T3$_t$ cells. The antibody was incubated with the cells on ice for 1 hour. The cells were washed twice with cold FACS buffer, and 100 µl of a FITC-conjugated goat anti-mouse secondary antibody was added. After 1 hour on ice, the cells were washed twice with FACS buffer and resuspended to 500 µl with 10% neutral buffered formalin. The resuspended cells can be stored wrapped in foil for up to 2 days at 4° C. The labeled cells were analyzed in a Coulter EPICS 541 flow sorter and a mean peak channel fluorescence determined for 5000 cells. The mean peak for reactivity to NIH3T3$_t$ cells was compared to the mean peak for reactivity to NIH3T3 cells. For antibodies reacting with the external domain portion of gp185, the peaks were non-overlapping.

Antibody Assays

Polystyrene plates (96-well) were coated with 100 ng of a lysate from c-erbB-2 expressing cells diluted in PBS. The lysate was prepared by adding 2-3 ml cold lysis buffer (0.15 M NaCl, 0.1% Triton X-100, 0.1% deoxycholate, 0.1% SDS, 10 mM Tris pH 7.4, 1 mM PMSF) to 2×10$^6$-1×10$^7$ cells and incubating on ice for 15 minutes. Lysates were centrifuged at 10,000 g for 20-30 min and supernatants were assayed for protein, aliquoted and stored at −20° C. The plates to which lysate was added (referred to as the competition plates) were incubated overnight at room temperature and then washed with PBS. Another 96-well plate (incubation plate) was blocked with 1% BSA in PBS (100 µl/well) for 1 hour at room temperature. These plates were washed and antigen (either supernatants from gp75 expressing CHO cells, mouse sera, or cell lysate preparations) was mixed with TAb 251 at 5 ng/ml in the wells, and the plates were incubated for 2-4 hours at room temperature. The competition plates were similarly blocked with 1% BSA/PBS and washed and 100 µl of the incubation mixture was transferred from the incubation plates to the competition plate and incubated 1 hour at room temperature. The plates were then washed with PBS/0.05% Tween 20 and a biotinylated goat anti-mouse IgG antibody was added at 1:400 dilution (vol/vol), 100 µl per well. The plates were incubated 30 minutes at room temperature, washed and 100 µl of a Strepavidin-HRP conjugate was added at 1:8000 dilution (vol/vol). After an additional 30 minute incubation at room temperature, followed by an ash step as described above, the TMB substrate was added at 100 µl/well. This substrate was prepared immediately before use by mixing 5 ml. TMB stock (1 mg/ml 3, 3', 5, 5' tetramethylbenzidine in methanol) with 5 ml citrate buffer, pH 4.5 and 4 µl 30% hydrogen peroxide. After a 15 minute incubation in the dark at room temperature, the absorbance was measured at 450 nm. The TAb 251 preincubated with PBS was used as an uncompeted control to determine maximum binding to lysate coated competition plates.

ELISA Assays

Polystyrene 96-well plates were pretreated for 2 hours at 37° C. with bovine collagen at 1 mg/ml in sterile PBS at 100 µl/well. NIH3T3 or NIH3T3$_t$ cells were grown to 80% confluency in DMEM+4% FBS, harvested with warm Puck's Versene, washed and plated overnight at 37° C. at 1×10$^6$ cells/ml, 100 µl/well in the previously treated and washed collagen plates. Plates were gently washed and treated for 1 hour with 100 µl of 10% neutral buffered formalin. The plates were again washed with PBS, and blocked with 1% BSA in PBS for 1 hour at 37° C. Sample supernatants or antibody dilutions were then added to the coated, blocked and washed plates at 100 µl per well and the plates were incubated for 2 hours at 37° C. After another PBS wash step, 100 µl of a 1:500 dilution of an alkaline phosphatase-conjugated goat anti-mouse IgG Fc-specific secondary antibody was added and the plates were incubated for 1 hour at 37° C. After a final PBS wash, a BioRad substrate (PNPP+diethanolamine) was added, and after a 10-15 minute incubation at room temperature, the absorbance was measured at 405 nm.

Immunoperoxidase Staining

The immunoperoxidase staining procedure used was a modification of the avidin-biotin immunoperoxidase technique of Hsu et al., *J. Histochem. Cytochem.*, 29, 577-580 (1981) as described by Horan-Hand, et al. *Cancer Res.*, 43, 728-735 (1983), both of which articles are herein incorporated by reference.

The following examples are presented to help in the better understanding of the subject invention and for purposes of illustration only. They are not to be construed as limiting the invention in any manner.

EXAMPLE 1

Expression of c-erbB-2 in CHO Cells c-erbB-2 Vector Construction

A 2.0 kb fragment of the c-erbB-2 cDNA encoding the extracellular domain of the putative c-erbB-2 protein was excised from the Okayama-Berg cloning vector, pSV7186

Figure 3:
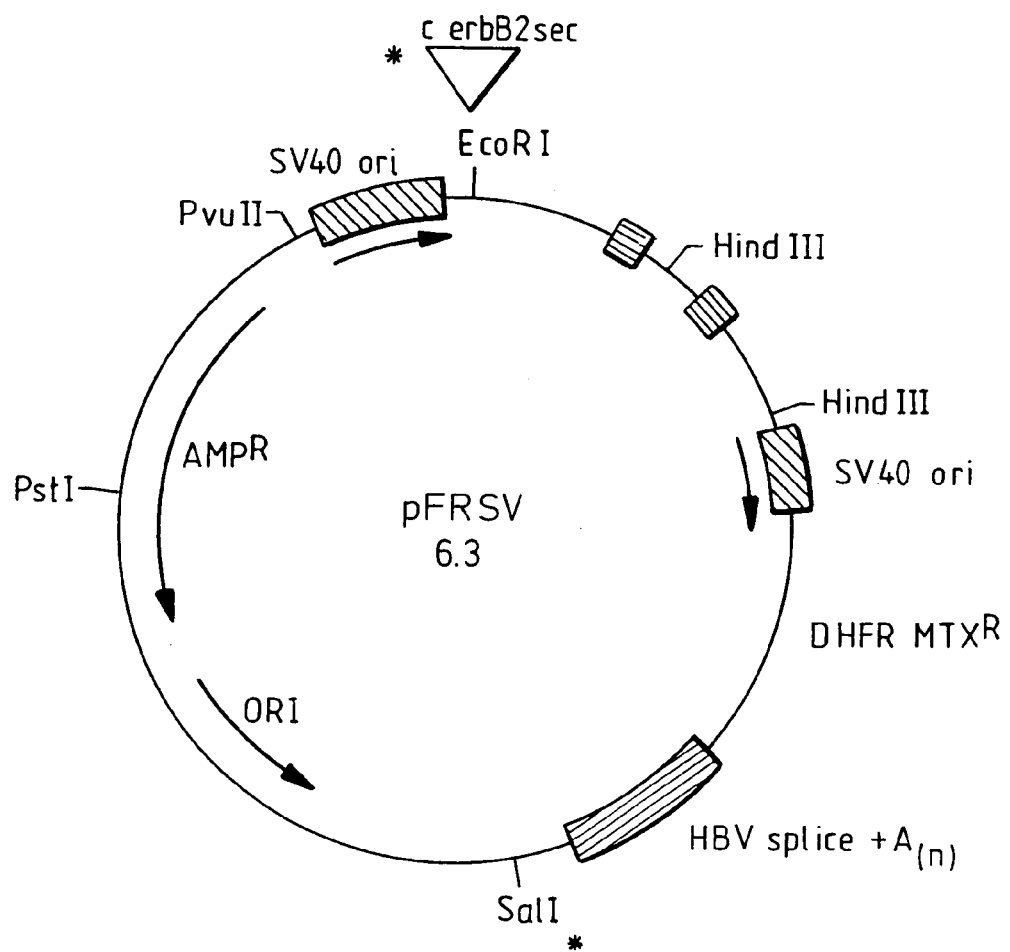
FIG. 3 shows a partial restriction map of the cloning vector, pFRSV. This vector contains a transcription unit driven by an SV40 early region promoter and origin, as well as the SV40 large T antigen intervening sequence (5' mRNA splicing) and early region polyadenylation site. A second transcription cassette contains a mutant DHFR gene, the dominant selectable marker encoding resistance to methotrexate (MTX). The 2.2 kb c-erbB-2sec fragment was subcloned into the unique EcoRI site located downstream from the first SV40 ori/promoter to generate pFRSV-c-erbB-2sec.

(available through Pharmacia, cat. #27-4948-01) using NcoI and AatII, blunt-ended using T4 DNA polymerase, and ligated with EcoRI linkers (NE Biolabs, cat. #1078). The initial c-erbB-2 cDNAs were isolated by D. Slamon (UCLA) and were derived from a female patient with adenocarcinoma of the breast (see FIG. 16 for the complete nucleotide sequence for c-erbB-2). The EcoRI-linkered partial c-erbB-2 cDNA was then subcloned into EcoRI digested pFRSV, an SV40-based derivative of pFR400 (Horwich et al. 1985). To construct pFRSV, a 2.6 kb PvuII/HpaI fragment was isolated from pKSV10 (commercially available through Pharmacia, cat #27-4926-01), and blunt-end cloned into PvuII-digested pFR400. The BglII site at nucleotide position 5107 of pKSV-10 had previously been converted to an EcoRI site by site-directed mutagenesis (Zoller and Smith 1987) leaving a unique RI cloning site in the final construct, pFRSV. This vector also contains the dominant selectable marker, DHFR, which was utilized for amplification of the gp75 c-erbB-2 derivative. The final construct, designated pFRSV-c-erbB-2sec (FIG. 3) was transformed into $E.$ $coli$ strain, MC1061, and plasmid DNA was isolated according to Maniatis et al. 1982.

Transfection of pFRSV-c-erbB-2sec

Transient expression of the plasmid was monitored using COS7 cells and calcium phosphate ($CaPO_4$)-mediated transfection (Graham and van der Eb 1973). Cells were split 1:10 onto 100 mm tissue culture dishes 24 h prior to transfection (app. 30-50% confluency). 20 μg (in 10 μvol) of the plasmid construct in 0.49 ml 2×HeBS was mixed with 0.5 ml of 0.25 M $CaCl_2$. [see Ausutel et al. (eds.) 1988)] which was slowly bubbled into the DNA/HeBS mix, vortexed for 10 sec, and then allowed to stand at room temperature for 20-30 min to allow for formation of the DNA precipitate. This precipitate was then added to the dish of COS7 cells, and the cell/precipitate mix was incubated at 37° C., 5% $CO_2$ for 15 h. The precipitate washed from the cells with phosphate-buffered saline (Gibco), incubated in complete growth medium (DMEM) and assayed for expression of c-erbB-2 48 h following introduction of the DNA.

Stable expression of pFRSV-c-erbB-2sec was obtained in CHO cells after using $CaPO_4$-mediated transfection (see above). The DNA precipitates were made exactly as described above using 20 μg of plasmid DNA and four 100 mm dishes of CHO cells. Each transfected 100 mm dish was split 1:20, 72 h following introduction of the plasmid, and cultured for 18 days in α-MEM (lacking nucleosides and nucleotides) containing 10% dialyzed fetal bovine serum and 20 nM MTX. Stepwise amplification was initiated, cells were passaged every 6 days into increasing concentrations of MTX (100 nM, 2.5 μM, 12.5 μM and 50 μM). These MTX-resistant populations were cloned by limiting dilution following 21 days of growth in MTX. $10^6$ cells from one of these populations were diluted in growth medium (see above) as follows: 2×, 1:100, then 2×1:10, resulting in approximately 1 cell/well of a 96 well microtiter plate (Costar). The cells were maintained in 50 μM MTX and expanded successively into 24- and 6-well microtiter plates, followed by 60 mm dishes over a period of three weeks. The MTX-resistant clones were then assayed for gp75 expression by radioimmunoprecipitation, immunofluorescence, and Western blot.

Immunofluorescence

Cellular localization of gp75 was detected using anti-c-erbB-2 TAb 252 or the supernatant from the parent hybridoma thereof A29. (See Methods above for methods of preparing said MAbs.) Cells were unadhered with PBS/5 mM EDTA, washed 2× with PBS, and fixed in 2 ml 4% p-formaldehyde/PBS for 10 min at 37° C. Cells were washed in PBS, incubated in 0.6% n-octyl-glucoside/PBS for 5 min at RT to permeabilize membranes, and then resuspended in 1×HBSS containing 2% FBS and 10 mM HEPES, pH 7.0 containing 10 μg/ml of either of the anti-c-erbB-2 MAbs. This incubation with the primary antibody was performed on ice for 60 min, followed by two washes in PBS. Cells were then resuspended in 100 μl of HBSS containing FITC-F (ab')$_2$ anti-mouse IgG (Tago, Inc., Catalog #4950). Transfected cells were also stained with a non-specific urine myeloma IgG1 (Litton Bionetics).

Radioimmunoprecipitation (RIP)

Transiently transfected or stably expressing c-erbB-2sec cells were grown in 60 mm dishes to 80% confluency, and then starved in 2 ml cystine-free media for 1 h. Cells were then labeled with 200 μCi $^{35S}$-cysteine (specific activity=600 Ci/mmol; Amersham) for 15 h at 37° C., 5% $CO_2$. The supernatants were then harvested and stored in 1 mM PMSF at −20° C. The cells were washed 2× in cold phosphate-buffered saline and lysed in 0.4 ml. 1×RIPA buffer [0.15M NaCl, 1% Triton X-100 (10 ml/L), 1% Na deoxycholate (10 g/L), 0.1% SDS (1 g/L), 10 mM Tris pH 7.4, 1 mM PMSF] per dish. After preclearing the lysates with protein A-sepharose (60 μl per 400 μl of lysate), 10 μl of the lysates were TCA precipitated to check for uptake. The lysates were then normalized for 4×$10^6$ counts per sample and incubated overnight with the antibody at 4° C. on a rocker. The supernatants were concentrated and equivalent amounts were incubated overnight with the antibody (4° C. on a rocker). After overnight incubation, samples were precipitated with 60 μl of protein A-sepharose for 30 min. at 4° C. and then spun down and washed with 1×RIPA four times. The adsorbed immunocomplexes were, after final wash, resuspended in 35 μl of 2× Laemmli buffer, boiled 5 min. and electrophoresed through a 7% acrylamide gel. The gel was then fixed, dried and exposed overnight.

For the Western blot, a 7% SDS-acrylamide gel was run and blotted with Tris-glycine-methanol buffer onto nitrocellulose. Blocking and incubation was done in 10% milk and 2% BSA. The method of detection was biotin-avidin with DAB as the substrate (diaminobenzidine tetrahydrochloride in 0.1M Tris, 0.02% hydrogen peroxide). The blot washed with a 0.05M Tris, 0.25M sodium chloride (NaCl), 3 mM EDTA, 0.05% Tween 20 solution.

Detection of the Soluble c-erbB-2 Derivative (gp75) in CHO Cells

The pfRSV-cerbB-2sec construct was introduced stably into CHO dx11 as described above, and reactivity with anti-c-erbB-2 TAb 252 was examined in both cell lysates and supernates following the step-wise increase in MTX concentration, resulting in the anticipated amplification of gp75. Using RIP analysis as elaborated previously, the major portion of gp75 was detected surprisingly in cell lysates; a substantially lesser amount was observed from the supernatants of the stably expressing gp75 CHO population. Immunofluorescence was performed to aid in determining why this should occur since the construct did not contain a hydrophobic transmembrane domain, and, thus, should have been secreted into the supernatants of the gp75 stably transfected CHOs. Immunofluorescence analysis revealed roughly 30% of one transfected CHO population and 10% of a second population were reactive with the anti-c-erbB-2 TAb 252 and the protein did not appear to be localized to any particular organelle egs. lysosomes, nucleus. We assumed that that we could increase the secreted fraction of gp75 by limit dilution cloning of either of the gp75-expressing CHO populations. Individual MTX-resistant (50 µM) clones were obtained, expanded, and assayed for gp75 expression using the anti-c-erbB-2 TAb 252. Immunofluorescence analysis, RIP analysis and Western analysis confirmed the successful cloning and expression of gp75. Expression levels of secreted gp75 from CHO clones were approximately 10-20 fold greater compared with the uncloned populations.

Figure 4:
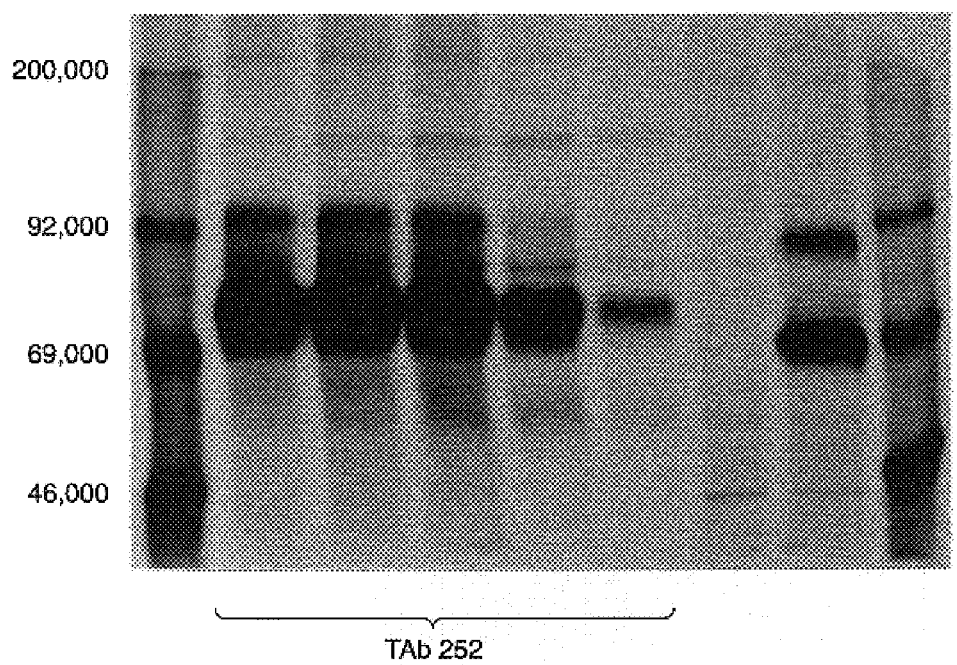
FIG. 4 is a SDS-PAGE wherein the lanes were loaded as follows: Lanes 1 and 9: Std; Lanes 2-6: A soluble fragment of c-erbB-2 expressed by NIH3T3 c-erbB-2 transfectants competes with gp75 for binding to anti-c-erbB-2 TAb 252; Lanes 2-6: Increasing amount of cell lysate from NIH3T3-c-erbB-2 were incubated for 7 h with 10 μg anti-c-erbB-2 TAb 252, followed by 10 h incubation of 400 μl of in vitro labeled supernatant collected from gp75-expressing CHO cells; Lane 7: Lysate from in vitro labeled gp75 CHO clone immunoprecipitated with isotype matched non-specific control, mouse myeloma mAb, (IgG1); Lane 8: Lysate from CHO-gp75 immunoprecipitated with TAb 252.

To examine the possibility that a 'soluble' derivative of c-erbB-2 might occur in vitro, competition for binding to an anti-c-erbB-2 TAb 252 recognizing an extracellular epitope was performed. The two cell types used for this experiment were NIH-3T3 stably transfected with a full length c-erbB-2 cDNA (King et al., 1985) and one of the gp75-expressing CHO clones described above. Supernatant was collected from the clone which was previously in vitro labeled using $^{35}$S-cystine. Competition was performed using a constant amount of anti-c-erbB-2 antibody TAb 252, a constant amount of labeled gp75-CHO supernatant with increasing amounts of 3T3-c-erbB-2 unlabeled cell lysate. SDS/PAGE revealed that as the concentration of unlabeled 3T3-c-erbB-2 (gp185) increased, the intensity of the RIP band at approximately 75 Kd decreased proportionally (FIG. 4). This strongly suggested that a soluble form is 'released' from cell types expressing a membrane-bound form of this protein, and there is apparent heterogeneity in glycosylation among different cell types. The supernatant from the gp75 expressing CHO cells competed the binding to the NIH3T3$_t$ lysate (FIG. 4).

EXAMPLE 2

Purification of Recombinant c-erbB-2 Protein

Plasmid Purification

The plasmid DNA was amplified in a one liter culture of bacteria by adding 200 µg/ml chloramphenicol to the cells at OD 600=0.8. After overnight incubation at 37° C., the bacteria was pelleted and resuspended in 10 ml of 50 mM sucrose, 25 mM Tris-Cl (pH 8.0) and 10 mM EDTA. Another 10 mls of this solution with 10 mg/ml lysozyme was added and incubated at room temperature for 10 min. 40 mls of a 0.2M NaOH, 1% SDS solution was slowly added into the mix and incubated on ice for 10 min. Then 30 mls of 3M sodium acetate pH 5.0 was added and the mixture was incubated another 10 min. on ice before centrifugation at 20,000 rpm for 20 min. at 4° C. in a Beckman SW27 or equivalent. The supernatant was precipitated with an equal volume of isopropanol at room temperature for 20 min., and the precipitate spun down in a Sorvall at 12,000 g for 30 min. at room temperature. The pellet was resuspended in 2.4 ml TE buffer (10 mM Tris-Cl pH 7.4, 1 mM EDTA) and mixed with 4.2 g cesium chloride (CsCl) and 0.4 ml ethylene bromide (EtBr) (10 mg/ml). The sample was then loaded into a 5/8×3 in. Beckman Quick-Seal polyallomer tube beneath a layer of CsCl solution, approximately 8 mls, (density=1.470 g/ml, n=1.3780) and spun at 50,000 rpm in a Sorvall T127 for 18 hours at 20° C.

Preparation of Immunoaffinity Gel

Monoclonal antibody TAb 254 (See Methods above for preparation of said MAb) was coupled to an NHS activated affinity gel (Affi-Prep 10; Bio-Rad Labs, Richmond, Calif.) according to the manufacturer's directions. Briefly, 4.5 mg of purified antibody was exchanged into Coupling Buffer (20 mM HEPES, pH=7.5, 150 mM NaCl), then concentrated by ultrafiltration to a final volume of 1.0 ml. This solution was added to 2.0 ml of gel pre-equilibrated in ice cold Coupling Buffer, and the slurry was mixed overnight at 4° C. After coupling, the gel was collected on a scintered glass funnel and washed with Coupling Buffer. Samples of the filtrates were assayed for protein using a BCA protein assay (Pierce, Rockford, Ill.). The total protein recovered in all filtrates was 1.2 mg. It was, therefore, assumed that 3.3 mg of IgG was coupled to the gel.

Remaining reactive sites were blocked with 2-aminoethanol. 5.0 ml of a 100 mM 2-aminoethanol solution in Coupling Buffer, pH=8.5, was added to the gel, and the slurry was mixed at room temperature for two hours. The gel was then washed extensively with PBS and stored at 4° C. Sodium azide was added (final concentration of 0.02% w/v) to inhibit bacterial growth.

Isolation and Purification of the c-erbB-2 Extracellular Domain

Starting material for the purification of soluble c-erbB-2 extracellular domain protein was a 10-fold concentrate of the transfected CHO supernatant. The concentrated supernatant was thawed and protease inhibitors were added to the following final concentrations: 0.2 mM PMSF, 2.1 µg/ml aprotinin, 2.5 µg/ml pepstatin A, 1.0 µg/ml leupeptin, 2 mM EDTA, 2 mM EGTA. The pH of the supernatant was adjusted to 7.0 with 1.0 N sodium hydroxide (NaOH).

In some experiments, the supernatant was concentrated another 4-fold by ultrafiltration. Additional concentration caused the supernatant to become turbid, and this turbidity was removed prior to chromatography by centrifugation (10,000×g, 20 min.).

The supernatant was filtered through a 0.45 µm membrane, then loaded on a 0.5×5 cm column packed with the 254 immunoaffinity gel (1.0 ml bed volume). The column was loaded at a flow rate of 0.2 ml per minute. Nonspecifically bound material washed away with 10 mM sodium phosphate, pH=7.0, 500 mM sodium chloride (NaCl). Washing was continued until a stable baseline absorbance at 280 nm was reached. Specifically bound material was then eluted with a step gradient of 100 mM glycine-HCl, pH=2.5, at a flow rate of 0.2 ml/min. 1.0 ml fractions were collected. The column was then washed extensively with PBS. Loading, washing, and elution were carried out at 4° C. (FIG. 1).

Figure 2A:
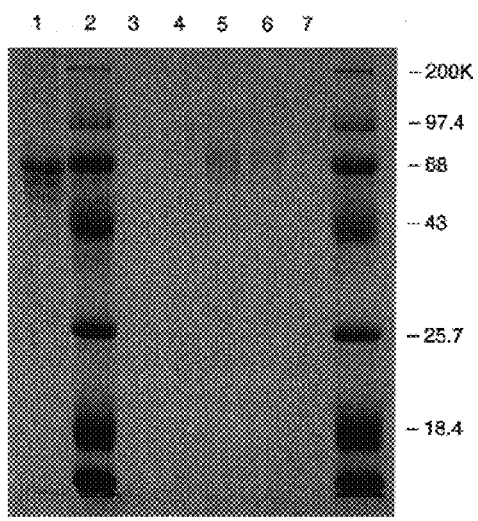
FIG. 2A is a SDS-PAGE of immunoaffinity column fractions of recombinantly produced c-erbB-2 gp75, as described above for FIG. 1. Samples of each fraction were prepared in Laemmli sample buffer and run on a 10% polyacrylamide gel. The gel was stained with Coomassie blue R-250.
Figure 2B:
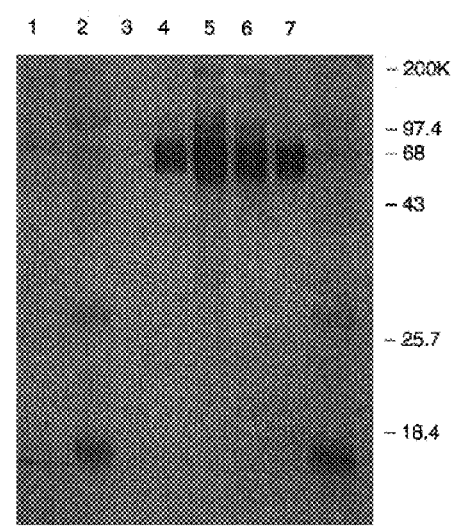
FIG. 2B is a Western blot. A gel identical to that run in FIG. 2A was run, and the separated proteins were electrophoretically transferred to a 0.22 μm nitrocellulose membrane. The membrane was probed using rabbit polyclonal antibody raised against an E. coli expressed recombinant fragment of gp185 (antibody 92A). Specifically bound antibody was visualized using goat anti-rabbit horseradish peroxidase conjugate and Indophane substrate (Vio-medics, Worcester, Mass.). The lanes were loaded as follows: Lane 1: concentrated CHO supernatant; Lane 2: prestained molecular weight standards (Bethesda Research Laboratories, Gaithersburg, Md.); and Lanes 3-7: immunoaffinity column fractions 1-5 (as indicated in FIG. 2A).

The presence of c-erbB-2 protein in the column fractions was determined by SDS-PAGE and Western-blot analysis (FIGS. 2A and B). For Western blot analysis, antigen was detected using polyclonal antibody 92A (see Methods above for its preparation) (purified IgG fraction) at a 1/2000 dilution (vol/vol). Fractions containing peak reactivity were pooled and dialyzed against PBS containing the protease inhibitors listed above. The dialyzed pool was then concentrated by ultrafiltration. Final protein yield was determined by BCA protein assay using bovine gamma globulin (Bio-Rad Labs, Richmond, Calif.) as a standard.

Total protein yield from one chromatography cycle was about 90 µg. This represented approximately 90% of the antigenic activity in 500 ml of 10× concentrated supernatant, as determined by IRMA. Five loading and elution cycles were carried out on the same column without an apparent loss in antigen binding capacity. SDS-PAGE analysis of the eluent pool revealed two closely spaced bands at approximately 75 kD and a minor band at 90 kD. These differences in size are probably due to differential glycosylation and/or proteoylsis of the protein.

EXAMPLE 3

Immunoradiometric Sandwich Assays (IRMA)

TAbs 251 and 255-265 were radiolabeled using the Iodogen method to a specific activity of 10-20 µCi/µg. Immulon I removal 96-well plates were coated with one of the following TAbs: 251, 255-265, at 10 µg/ml in pBS at pH 7.2 overnight at 4° C. The plates were then washed with PBS, blocked with 1% BSA in PBS for 1 hour at 37° C. After an additional wash step, 100 µl of the samples (either cell lysates or supernatants, partially purified gp185 or gp75 proteins, or serum samples) diluted in PBS were added to the TAb-coated wells and the plates were incubated for 2-5 hours at 37° C. The plates were washed and 100 µl of the radiolabeled tracer antibody (adjusted to 200,000 cpm/100 µl with 1% BSA in PBS) were added to the wells. After a 2-24 hour incubation at room temperature, the plates were washed and individual wells were counted in a gamma counter. Percent bound (1% B) was calculated using the following equation:

% $B$ = (cpm of sample/total cpm) × 100

For assays in which an affinity purified gp75 protein (from a transfected CHO cell line) was available, a sigcurve function was used to generate a standard curve from which unknown concentrations were determined in ng/ml gp75 equivalents from the fitted function.

Figure 7:
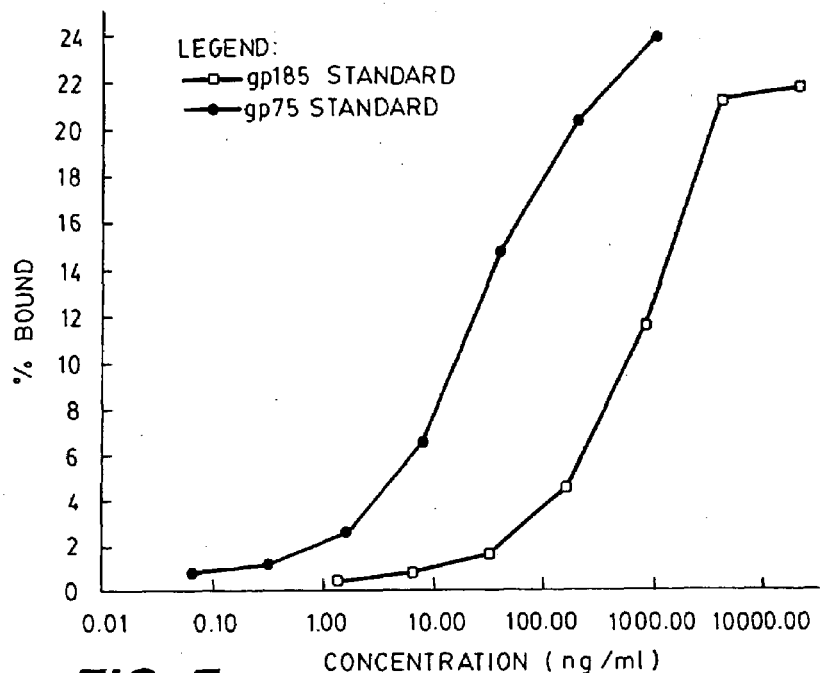
FIG. 7 shows standard curves of partially purified gp185 and gp75 proteins in the sandwich IRMA assay using TAb 259 as a capture antibody and TAb 256 as the radiolabeled secondary antibody. The assay is able to detect both the whole c-erbB-2 protein partially purified from transfected NIH3T3 cells as well as the external domain protein purified from the supernatant of transfected CHO cells. The assay is approximately 100× more sensitive when the partially purified gp75 is used as a standard.

Table 2 depicts which combinations of monoclonal antibodies were able to detect the gp75 protein in the sandwich IRMA format. Both a semi-purified gp185 as well as a gp75 standard were tested in two of the IRMA formats. Interestingly, one of these formats utilizing TAb 251 as a capture antibody and TAb 255 as a labeled antibody, was able to detect signals from c-erbB-2 expressing cell line lysates and the gp185 protein partially purified from NIH3T3 cells transfected with the c-erbB-2 oncogene, but was not able to detect the gp75 protein or a signal from nude mouse sera bearing c-erbB-2 induced tumors. This data, summarized in Table 3, along with data from the competition assay suggested that the final assay format would need to detect gp75 protein in order to also detect a signal in nude mouse sera. The final assay format with appropriate sensitivity and specificity for gp185 as well as gp75 consisted of TAb 259 as a capture antibody and TAb 256 as the tracer antibody. This assay detected the partially purified gp75 protein with a sensitivity of 0.5-1 ng/ml, detected a partially purified gp185, detected signals in cell lysates overexpressing gp185 and in nude mouse sera (summarized in Table 3). A standard curve for this assay showing increased sensitivity for the gp75 protein is depicted in FIG. 7. The TAb 256/259 IRMA assay was used to quantitate signals from cell culture supernatants. Cell lines, which are positive for the c-erbB-2 protein, shed an antigen which was detected and quantitated by this IRMA assay. Table 4 indicates that levels of shed antigen for a control NIH3T3 cell line are at background levels, whereas cell lines overexpressing gp185 and shedding a gp75 molecule in the supernatant as detected by radioimmunoprecipitation also shed an antigen detectable in the sandwich IRMA and quantitated at 22 to 70 ng/ml gp75 equivalents. The level of shed antigen depends on the level of c-erbB-2 overexpression as well as the confluency of the cultures.

This format was used to analyze and quantitate all mouse and human serum samples, and cell supernatants and cell lysates. Results from the competition and sandwich assays are summarized in Table 3, and indicate a correlation between the ability to detect the partially purified gp75 external domain protein and the ability to detect a shed antigen in serum samples from nude mice bearing c-erbB-2 induced tumors or in serum samples from human breast cancer patients.

TABLE 2

C erb B2 IRMA: Tested TAb Combinations

| Coating MAb | Tracer MAb | | | | | | | | | | | |
|---|---|---|---|---|---|---|---|---|---|---|---|---|
| | TAb 251 | TAb 255 | TAb 256 | TAb 257 | TAb 258 | TAb 259 | TAb 260 | TAb 261 | TAb 262 | TAb 263 | TAb 264 | TAb 265 |
| TAb 251 | − | − | − | − | − | − | − | + | +++ | + | ++ | − |
| TAb 255 | ++ | − | ++ | ++ | + | + | − | − | − | − | − | − |
| TAb 256 | − | − | − | − | − | ++ | − | − | +++ | − | ++ | − |
| TAb 257 | − | − | − | − | − | ++ | − | − | +++ | − | ++ | − |
| TAb 258 | − | − | − | − | − | − | − | − | +++ | − | ++ | − |
| TAb 259 | − | − | +++ | +++ | − | − | − | − | +++ | − | +++ | + |
| TAb 260 | − | − | − | − | − | − | − | − | − | − | − | − |
| TAb 261 | − | − | − | − | − | − | − | − | − | − | − | − |
| TAb 262 | + | − | + | + | − | +/− | − | − | − | − | − | − |
| TAb 263 | − | − | − | − | − | − | − | − | − | − | − | − |
| Tab 264 | +++ | ++ | +++ | +++ | +++ | +++ | − | − | − | − | − | ++ |
| TAb 265 | − | − | − | − | − | − | − | − | − | − | − | − |

− <5000 cpm at highest Standard
+ 5000 − 10,000 cpm at highest standard
++ 10,000 − 25,000 cpm at highest standard
+++ >25,000 cpm at highest standard

TABLE 3

Comparison of Competition and IRMA Assays in the Detection of External Domain of c-erbB-2 and Shed Antigen in Serum Samples

| | | | Assay Format | |
|---|---|---|---|---|
| Antigen | Source | Competition | 251/255 IRMA | 259/256 IRMA |
| Lysate | SKBR3 | + | ++ | ++ |
| Lysate | SKOV3 | + | ++ | ++ |
| Lysate | BT474 | + | ++ | ++ |
| Lysate | MCF7 | − | − | − |

TABLE 3-continued

Comparison of Competition and IRMA Assays in the Detection of External Domain of c-erbB-2 and Shed Antigen in Serum Samples

| | | Assay Format | | |
|---|---|---|---|---|
| Antigen | Source | Competition | 251/255 IRMA | 259/256 IRMA |
| Lysate | NIH3T3$_t$ | + | ++ | ++ |
| Lysate | NIH3T3 | – | – | – |
| Purified protein | 2-5% pure gp185 | + | ++ | ++ |
| Purified protein | 70% pure gp75 | + | – | ++ |
| Serum | Preimmune or normal | – | – | – |
| Serum | Nude mice bearing gp185 induced tumors | +/– | – | ++ |
| Serum | Human breast cancer | ND | ND | ++ |
| Serum | Human liver disease | ND | ND | – |

– No signal over background
+/– Weak signal over background
+ Detectable signal over background
++ Strong and quantifiable signal
ND Not determined

TABLE 4

Quantitation f c-erbB-2 Shed Antigen in Supernatants from Various Cell Lines Using the TAb 259/256 Sandwich IRMA Assay

| Cell Line | % Confluency | ng/ml gp75 Equivalents in Cell Culture Supernatant |
|---|---|---|
| NIH3T3$_t$ | 100 | 32.7 |
| NIH3T3 | 100 | 0.064 |
| SKBR3 | 100 | 70.0 |
| BT474 | 50 | 22.5 |

* Background level for media controls are 0.1 ng/ml

EXAMPLE 4

Nude Mouse Tumor Growth and Treatment

Balb/c nude mice were bled via tail vein prior to the start of the experiment. Animals were then injected (day 0) subcutaneously along the mid dorsum with $5 \times 10^6$-$1 \times 10^7$ NIH3T3$_t$ cells in 200 µl PBS. These cells were greater than 90% viable upon injection. The animals receiving treatment were injected 2-3 days after receiving cells (before tumor volume reaches 100 mm$^3$) with PBS, an IgG$_1$ control antibody or a TAb antibody at 100-500 µg/300 µl injected intraperitoneally every two-three days. Growth was determined by measuring length, width and height of the tumor using vernier calipers and calculating the volume in mm$^3$. Tumors were measured every 3 to 4 days. Animals were bled via tail vein every week to two weeks until the experiment was terminated at 28-31 days. At the end of the experiment, animals were terminally bled, the tumors were measured and excised for subsequent immunohistochemical studies.

Detection of Shed Antigen in Nude Mouse Sera

Figure 8:
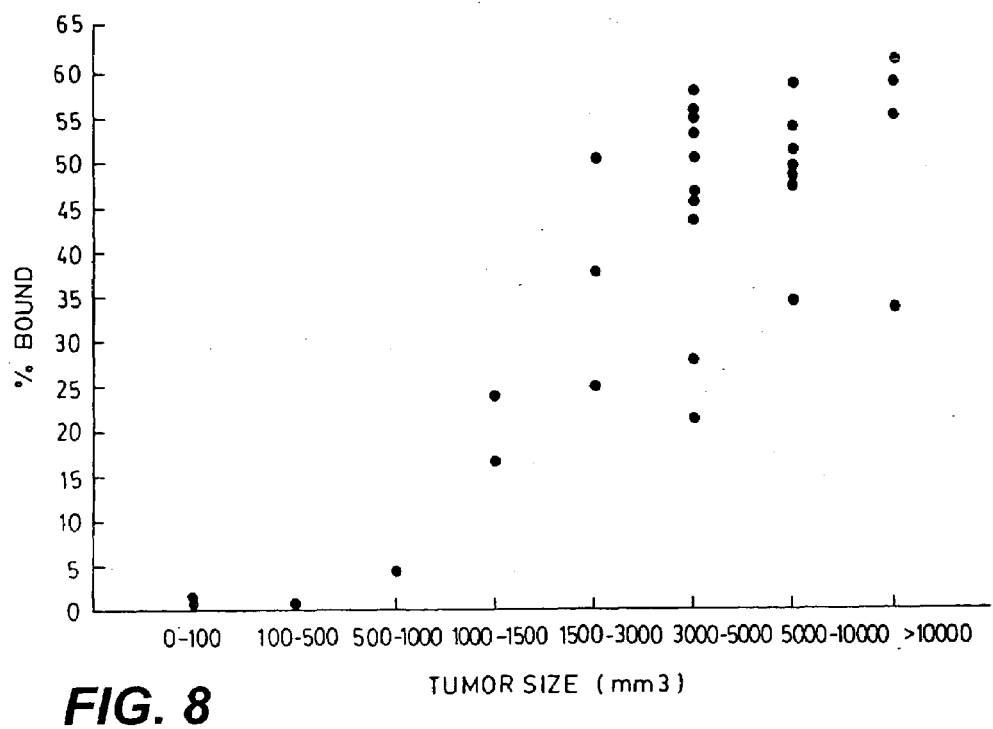
FIG. 8 shows the detection of a shed antigen in nude mouse sera bearing tumors induced by c-erbB-2 transfected NIH3T3 cells when tested in the TAb 259/256 sandwich IRMA assay. The sera are all tested at a 1:5 dilution (vol/vol) and background binding of a pretumor pool of sera in this assay is 1.7%. The standard curve using the gp75 protein for this assay is comparable to that shown in FIG. 7. Signals are detectable in mice with tumor sizes ranging from 500-1000 mm$^3$ and continue to increase until tumors reach 3000-10,000 mm$^3$.
Figure 9:
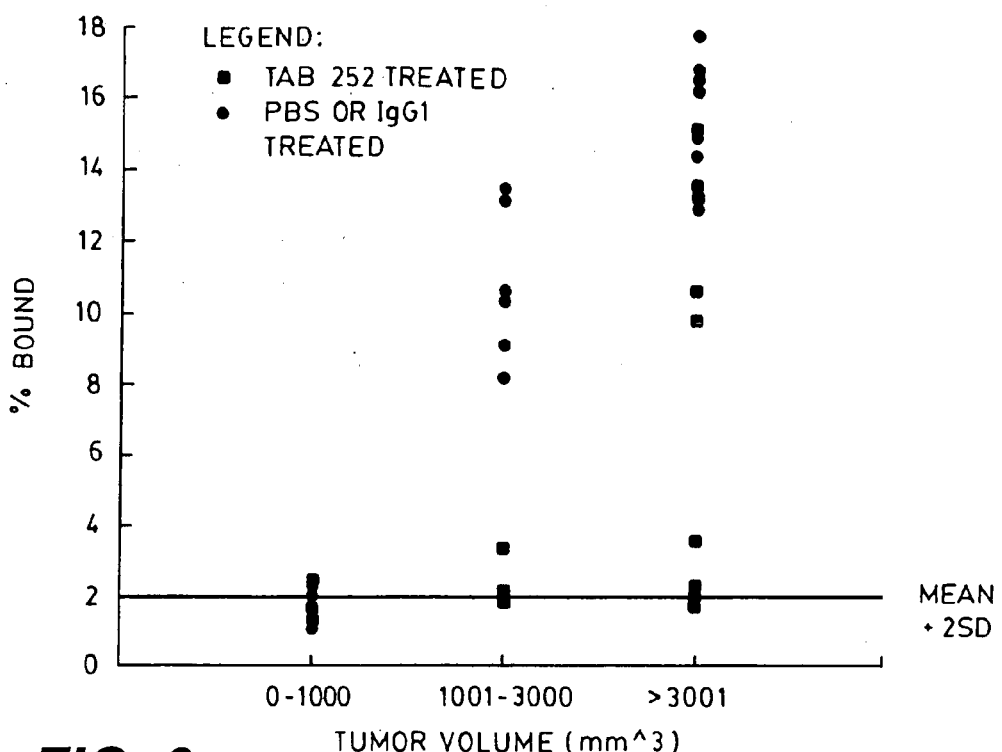
FIG. 9 shows analysis of nude mouse sera from mice bearing tumors induced by NIH3T3 cells transfected with the c-erbB-2 gene and treated with either TAb 252 or PBS or IgG1 and tested in the TAb 259/256 sandwich IRMA. The sera are from various bleed dates throughout the course of a one month experiment and are tested at a 1:5 dilution. The mice, at the time their sera are tested, have received 2-8 treatments (100-500 μg/treatment) of either TAb 252, a MAb reactive with the external domain of c-erbB-2, IgG1 or PBS. Six pretumor sera are tested in the assay and the mean binding determined. The background cut-off in the assay is determined as the mean of the pre-tumor sera+2 standard deviations above this mean or 2.2%. PBS-treated mice shed antigen which is significantly over background at tumor volumes of 1001-3000 mm$^3$ (n=7) while TAb 252-treated mice shed little detectable antigen at the same tumor volume (n=5). At larger tumor volumes the ability to detect shed antigen in sera from TAb-treated mice is still suppressed (n=9) as compared to sera from PBS-treated mice (n=8).

In FIG. 8, the percent bound signal in the IRMA assay of a 1:5 serum dilution (vol/vol) was graphed as a function of tumor size at the time the serum was drawn. These sera were from animals bearing tumors induced by the c-erbB-2 transfected NIH3T3 cells. The assay was able to detect an increasing signal with an increase in tumor size up to about 3000 mm$^3$, after which the signal plateaued. Due to very strong signals and limiting amounts of sera, the sera are analyzed at dilutions of 1/5 to 1/625 (vol/vol). Strong signals were frequently still observed at the highest serum dilution. When tumor bearing mice were treated with PBS or an IgG$_1$ control antibody, the signal detected by the IRMA assay was similar to untreated mice (FIG. 9). However, when animals were treated with a TAb recognizing the c-erbB-2 external domain, the amount of shed antigen detectable by the assay was severely suppressed at tumor sizes up to 3000 mm$^3$. Even in mice with tumor sizes >3000 mm$^3$, signals were suppressed in about half of the sera tested. These data suggest that an antibody recognizing the external domain of c-erbB-2, or a portion thereof, may suppress the level of detectable signal in the sandwich IRMA assay.

Human mammary or ovarian cell lines overexpressing the gp185 protein, grown in nude mice, also shed an antigen detectable in the c-erbB-2 IRMA assay as shown in Table 5. The signal correlates with increase in tumor size. MCF7 induced tumors remained small and did not shed a c-erbB-2 related antigen. The MDA468 cell line induced substantial tumor growth (>2000 mm$^3$) and had a substantial amount of EGFr but did not shed any antigen detectable by the sandwich IRMA assay (Table 5).

TABLE 5

Quantitation of Shed Antigen in Sera from Nude Mice Bearing Tumors Induced by High and Low c-erbB-2-expressing Human Cell Lines

| Sample/ Cell Line | gp185 expressing | Mouse | Tumor Volume (mm$^3$) | gp75 equivalents (ng/ml) |
|---|---|---|---|---|
| Pretumor | | | 0 | 0 |
| MCF7 | – | 1 | 195 | 0 |
| | | | 540 | 0 |
| | | 2 | 228 | 0 |
| | | 3 | 594 | 0 |
| MDA468 | – | 1 | 2436 | 0 |
| | | 2 | 3328 | 0 |
| | | 3 | 2700 | 0 |
| SKOV3 | ++ | 1 | 553 | 14.2 |
| | | | 920 | 10.3 |
| | | | 1625 | 29.4 |
| | | 2 | 1031 | 10.2 |
| | | | 2052 | 12.3 |
| | | 3 | 540 | 6.8 |
| | | | 891 | 5.0 |
| | | | 1250 | 10.0 |
| | | | 1260 | 7.7 |
| | | 4 | 2681 | 16.3 |
| | | | 4128 | 51.9 |
| MDA361 | ++ | 1 | 1924 | 28.1 |
| | | | 3391 | 34.4 |
| | | 2 | 3391 | 73.5 |
| | | | 4000 | 104.8 |
| | | 3 | 1211 | 18.6 |
| | | | 882 | 21.2 |
| | | | 1120 | 22.5 |
| | | | 1252 | 18.5 |
| | | | 1560 | 21.9 |
| | | | 1640 | 25.5 |
| | | 4 | 432 | 7.4 |
| | | | 400 | 7.8 |
| | | | 1309 | 12.2 |

Figure 13:
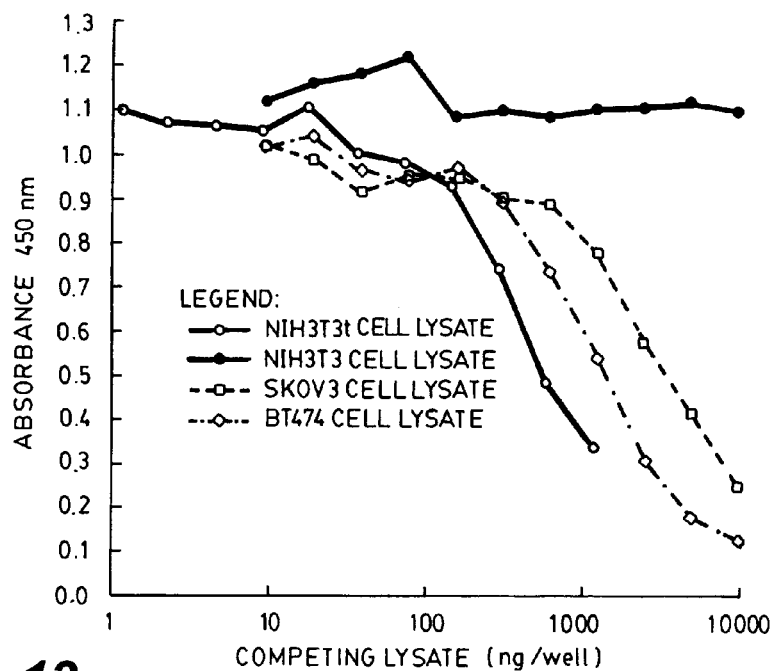
FIG. 13 shows competition assay results wherein the ability of various cell lysates to compete the binding of TAb 251 to a lysate from NIH3T3 cells transfected with the c-erbB-2 gene is tested. The SKOV3, BT474 and NIH3T3$_t$ lines all overexpress the gp185 protein and lysates from these lines compete with increasing protein concentration. A control NIH3T3 lysate fails to compete.
Figure 14:
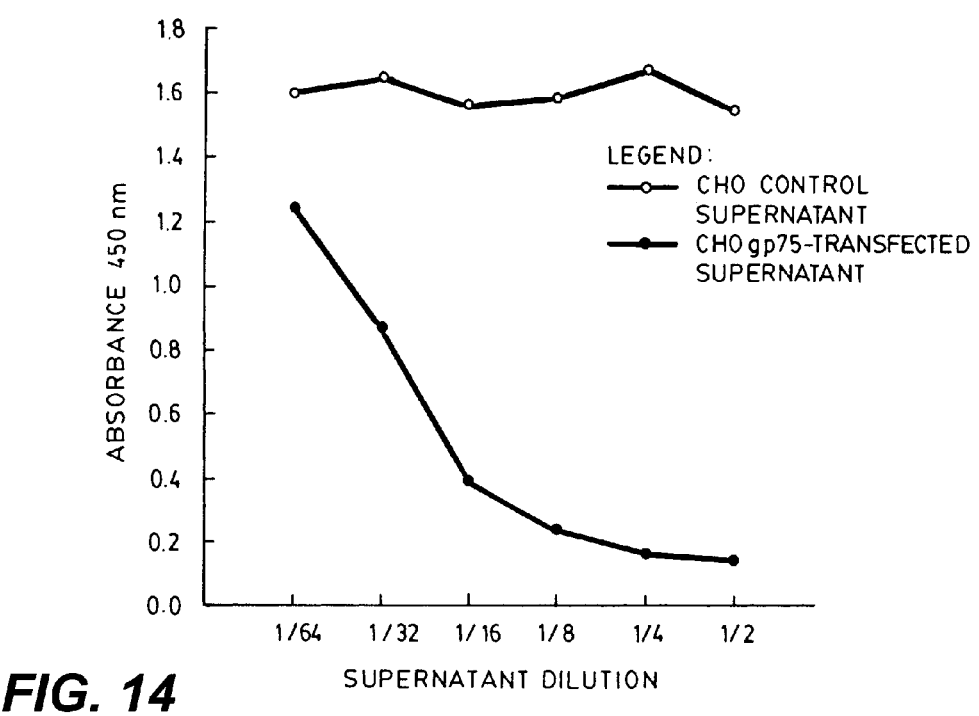
FIG. 14 shows results for a competition assay in which a supernatant from a CHO cell line transfected with the gp75 portion of the c-erbB-2 gene competes the binding of TAb 251 to a lysate from NIH3T3$_t$ cells. Supernatant from untransfected CHO cells fails to compete.

The competition assay was used to detect gp75 antigens which compete the binding of TAb 251, an ectodomain reactive MAb, with a lysate from transfected NIH3T3 cells. FIG. 13 demonstrates that lysates from cell lines expressing c-erbB-2 gp185, such as the human mammary cell line BT-474 and the human ovarian cell line SKOV3, can compete the binding to the NIH3T3$_t$ lysate comparable to the NIH3T3$_t$ lysate. The control 3T3 cell lysate that was not transfected failed to compete. Likewise, a supernatant from CHO cells transfected with the gp75 external domain is shown to compete the binding to the NIH3T3$_t$ lysate (FIG. 14) verifying that TAb 251 recognizes ectodomain and this binding alone is sufficient to compete the binding of the MAb to gp185.

Figure 15:
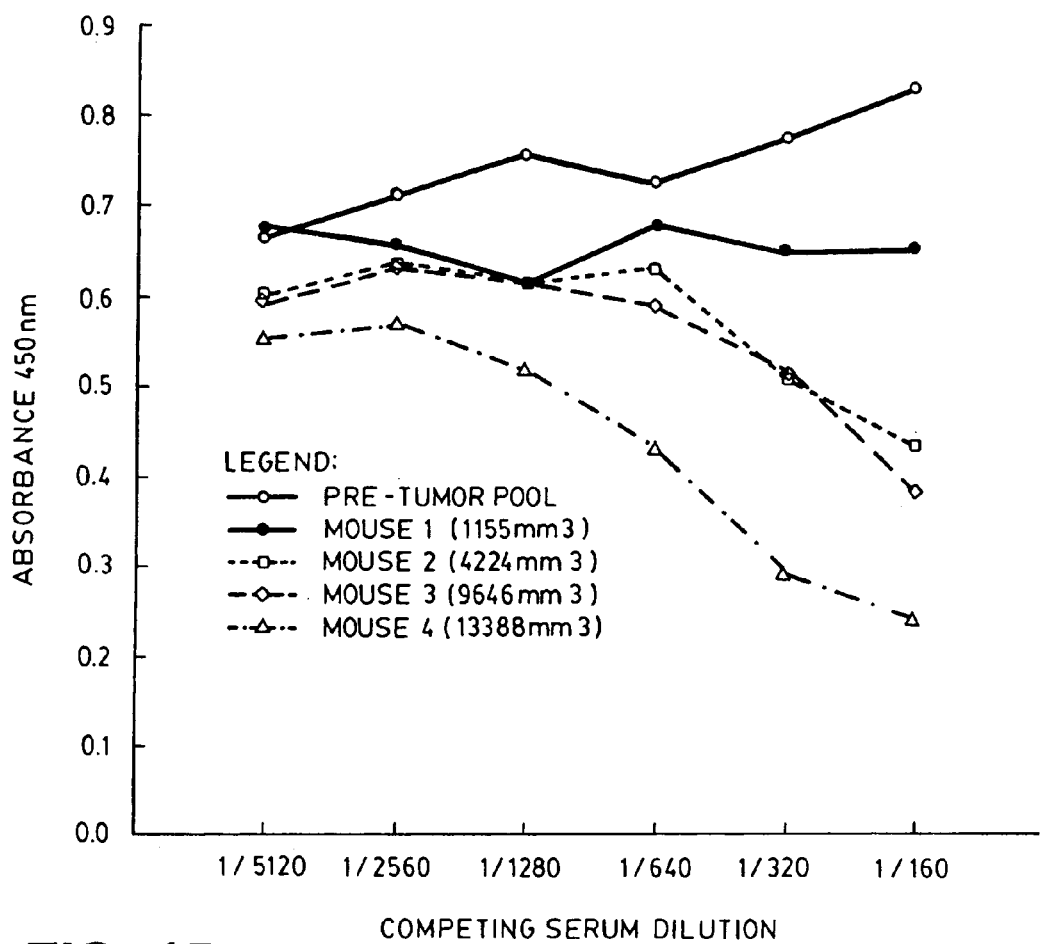
FIG. 15 shows test results indicating that nude mouse sera from animals bearing tumors induced by NIH3T3 cells transfected with c-erbB-2 are able to compete the binding of TAb 251 to a lysate from NIH3T3$_t$ cells. Mice 2-4 with tumor sizes greater than 1100 mm$^3$ are able to compete whereas mouse 1 serum and a pretumor pool of sera do not compete in the assay.

Nude mouse sera from mice bearing large tumors induced by the NIH3T3$_t$ transfected cells can compete the binding to the NIH3T3 (c-erbB-2 expressing cells) lysate as shown in FIG. 15. The ability to compete correlates with increasing tumor size; however, the assay is not sensitive enough to detect a signal distinct from non-specific interference at serum dilutions lower than 1/160 (vol/vol).

EXAMPLE 5

Detection of Shed c-erbB-2 in Human Tumor Cell Culture Supernate

Human breast tumor cell lines were cultured in T150 flasks and labeled with 400 µCi of 35S-cysteine in 15 ml of cysteine and methionine-free medium (Dulbecco's Modified Eagle's medium, DME H21, with 4.5 gm/l glucose). Cells were labeled overnight at 37° C. After 24 hours, the medium was removed, protease inhibitors added (Leupeptin 1 µg/ml, Boehringer Mannheim; Aprotinin 2.1 µg/ml, Sigma; Pepstatin A 2.5 µg/ml, Boehringer Mannheim; and PMSF 0.1 mM, Sigma), and then concentrated to 400 µl using an Amicon Centriprep 30.

Prior to immunoprecipitation, supernatants were stripped of non-specific protein A binding by incubation at 4° C. for 4 hours with 100 µl of a 50% slurry of protein A-sepharose beads. The beads and non-specifically bound material were removed by a 30 second spin in a microfuge, and supernatants were removed to new tubes. Antibody (20 µl containing approximately 10 µg) was then added, and the mixtures were incubated for 24 hours at 4° C. on a rotator. The following day, 50 µl of the protein A slurry was added to the sample which was incubated for 4 hours at 4° C. on a rotator. The beads were then pelleted for 30 seconds in a microfuge and washed five times with ice cold RIPA buffer (100 mM Tris-HCl pH 7.5, 100 mM NaCl, 0.5% TritonX-100, 0.5% deoxycholate, 10 mg/ml bovine serum albumin, 0.2 mM PMSF). Between the 3rd and 4th wash, tubes were changed. The final pellet was suspended in 50 µl of Laemmli sample buffer containing 1% beta-mercaptoethanol. Samples were heated to 75° C. for 5 minutes, spun for 30 seconds in a microfuge, and loaded onto a 7% SDS polyacrylamide gel.

The gels were stopped at approximately 120 ma-hrs and then fixed in 10% acetic acid, 30% methanol in distilled water for 45 minutes-1 hour. After a quick wash in distilled water, gels were soaked for 1 hour in 250 ml fresh distilled water. Gels were permeated with 250 mls EnHance (DuPont) for 90 minutes and equilibrated in 2% glycerol prior to drying onto filter paper. Dried gels were exposed to Kodak X-OMAT AR-5 X-ray film at −80° C. for one to three days.

Figure 5:
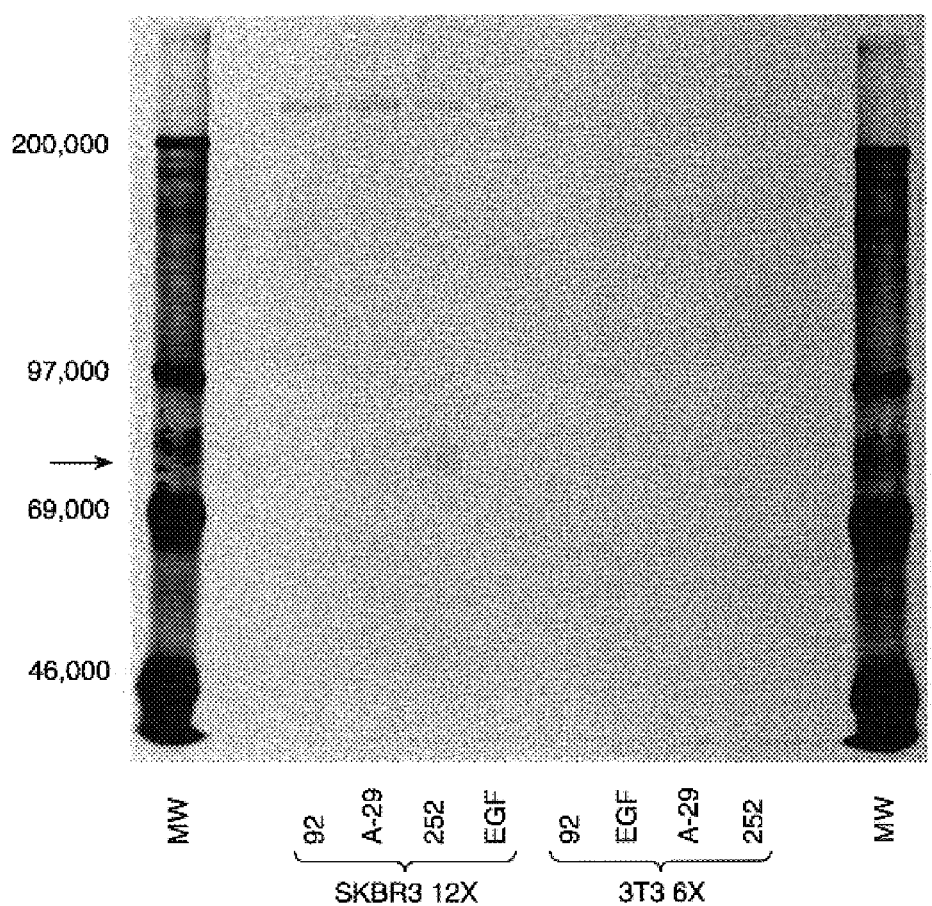
FIG. 5 shows the radioimmunoprecipitation of gp75 from tissue culture supernatants. Lanes 1 and 12: Molecular weight markers; Lanes 3-6: Supernatant from SKBR3 cells concentrated 12× and precipitated with 9.2 rabbit polyclonal—Lane 3; Lane 4: A-29 murine anti-c-erbB-2 hybridoma parent; Lane 5: TAb 252 murine anti-c-erbB-2 monoclonal; Lane 6: Amersham murine anti-EGF receptor monoclonal; Lanes 7-10: Supernatant from 3T3 cells transformed with the c-erbB-2 oncogene concentrated 6×; medium was not concentrated enough to visualize a precipitable signal.
Figure 6:
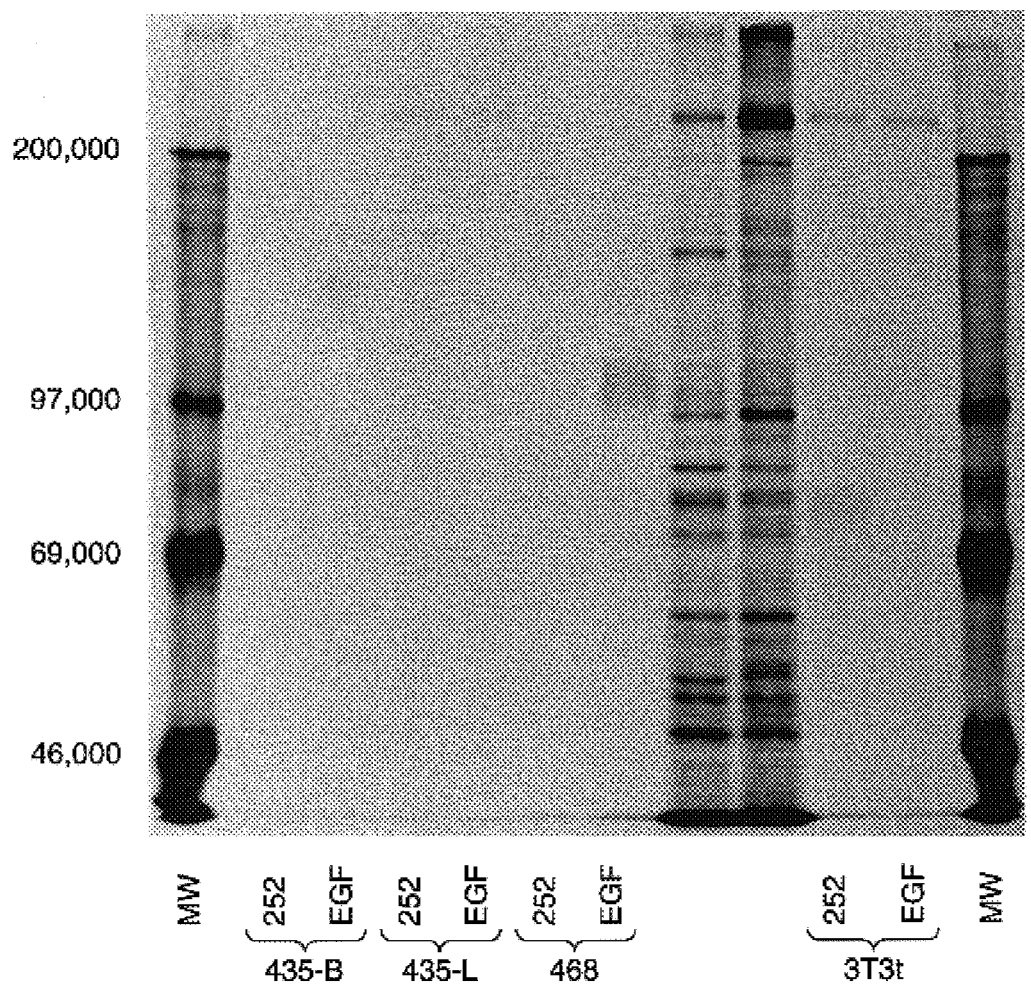
FIG. 6 shows the radioimmunoprecipitation of supernatants from c-erbB-2 positive and negative cell lines. Lanes 1 and 12: Molecular weight markers; Lanes 2 and 4: Supernatant from MDA435 concentrated 12× and precipitated with TAb 252; Lanes 3 and 5: The same supernate precipitated with Amersham anti-EGF receptor antibody; Lanes 6 and 7: 12× concentrated supernatant from MDA468 cultures precipitated with TAb252 and anti-EGF receptor antibody, respectively; Lanes 8 and 9: unrelated; Lanes 10 and 11: Control supernatant from transfected 3T3 cells concentrated 12× and precipitated with TAb252 and anti-EGF receptor, antibody.

Detection of the Soluble c-erbB-2 Derivative (Gp75) in the Media Supernatant of Human Tumor Cells FIG. 5 shows the autoradiogram of tissue culture supernatant from SKBR3 cells that was concentrated and precipitated with various antibodies. A distinct single band of approximately 75 kd was evident in those samples treated with c-erbB-2 antibodies (A29 and TAb 252) reactive with the extracellular domain. In contrast, no bands appeared in supernates treated with either a rabbit polyclonal antiserum made against a c-erbB-2 C-terminal peptide or with a monoclonal specific for the EGF receptor (Amersham). The specificity of the 75 kd band derived from SKBR3 cells was further demonstrated by the ability of the same monoclonal, TAb 252, to precipitate an identical molecular weight species from 3T3 cells transfected with the c-erbB-2 oncogene (FIG. 6). Also shown in FIG. 6 is the inability of TAb 252 to precipitate a 75 kd band from MDA468 supernate. That cell line expresses large quantities of EGF receptor, but does not express detectable levels of c-erbB-2. A larger molecular weight species of approximately 105 kd was precipitated from these cells with an anti-EGF receptor monoclonal. Precipitations were also done with supernatants from a third cell line, MDA435, that expresses neither c-erbB-2 nor detectable EGF receptor (FIG. 6), and no bands at either 75 or 110 kd were detected.

EXAMPLE 6

Detection of Shed Antigen in Human Sera

Figure 10:
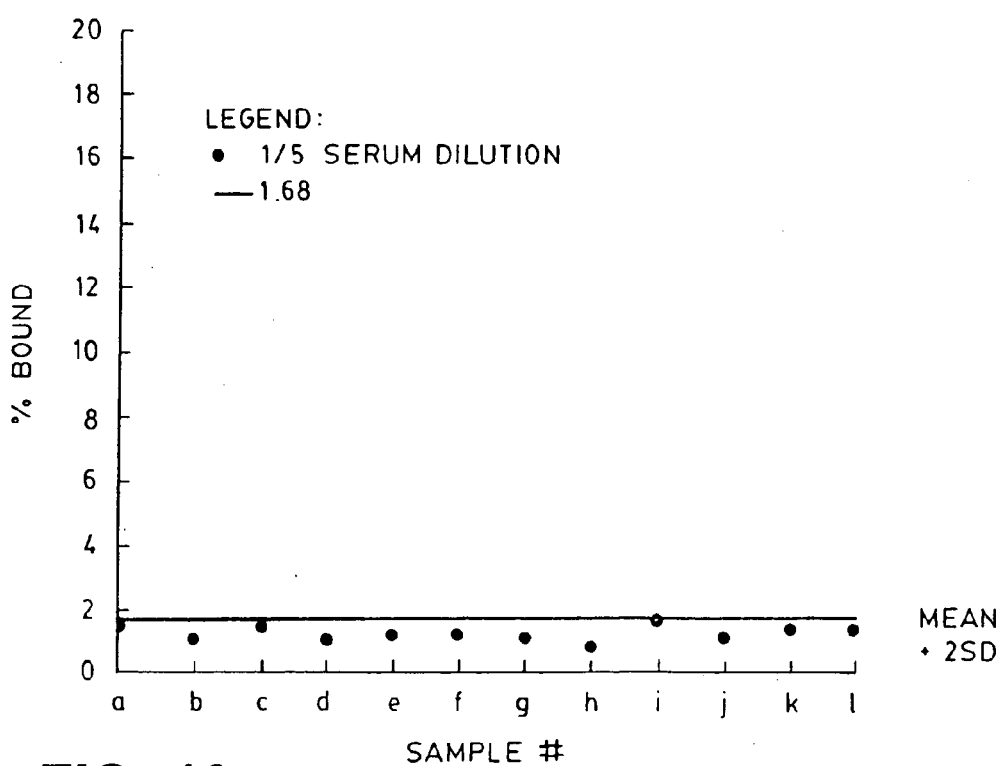
FIG. 10 shows test results for twelve human sera from normal volunteers in the TAb 250/256 sandwich IRMA assay at a 1:5 dilution (vol/vol). Using these sera, a background binding level of 1.68% is determined (mean+two standard deviations).
Figure 11:
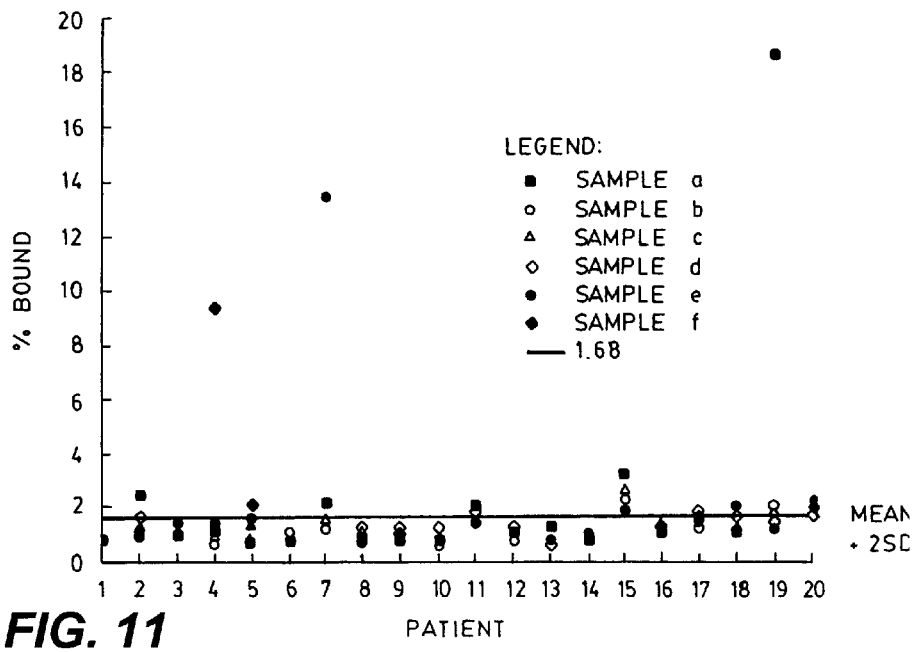
FIG. 11 shows test results for serial bleeds from twenty patients with breast cancer in the TAb 259/256 IRMA assay at a 1:5 dilution. The serial samples were taken throughout the course of the disease and therapy. For patients 1-4, sample [a] was taken at first diagnosis, one day before surgical removal of the tumor. Sample [a] for patients 5-10 was taken: several days after surgical removal of the tumor and sample [a] for patients 11-20 was taken at first or subsequent recurrence events. The remaining samples [b-f] (4 or 5 for each patient) were taken at various intervals throughout the course of therapy and do not correspond with a particular state of disease or response to therapy. Background cut-off for this assay was 1.68%.
Figure 12:
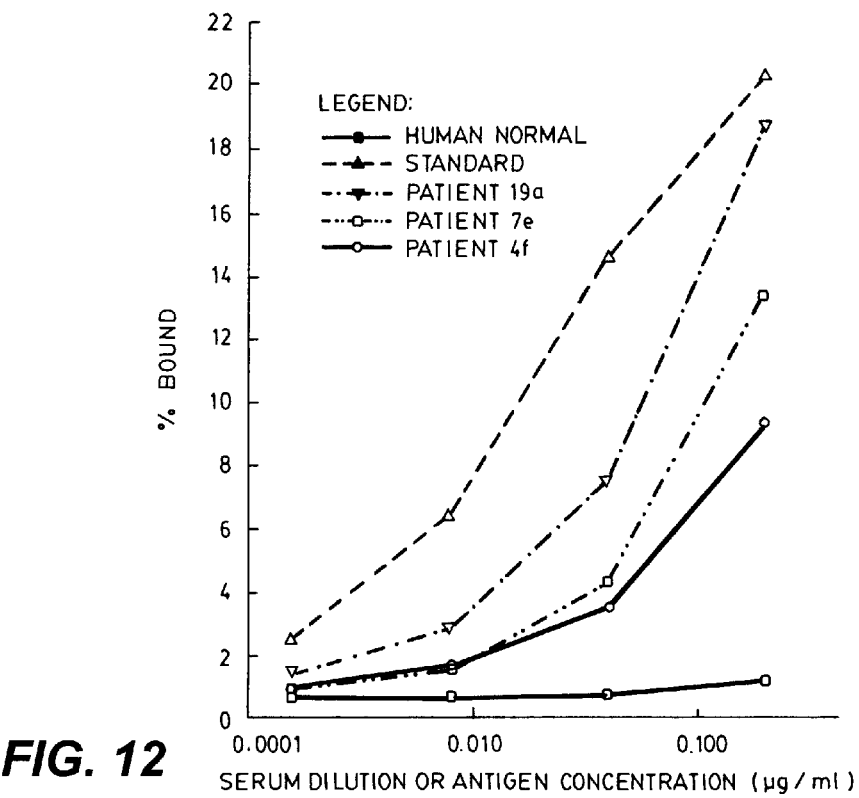
FIG. 12 shows the titration curve of three human sera from patients with breast cancer in the TAb 259/256 IRMA assay as compared to the gp75 standard and a normal human serum. The sera are all tested at a 1:5 dilution and background cut-off in the assay is 1.6%. For patient 19a, the serum sample was drawn when patient 19 presented with metastases approximately 1½ years after the primary tumor was removed. Patient 19 died 1½ years after this sample was taken. The 7e serum sample was drawn from patient 7 upon first failure with liver and bone marrow metastases seven months after the primary tumor was diagnosed. Patient 7 died six days after this last sample was drawn. The patient 4f sample was drawn at the time of first failure with liver and node metastases two years after the primary tumor was diagnosed. Patient 4 died six months after this [f] sample was drawn.

A panel of 20 human sera from breast cancer patients, on which sequential bleed dates were available, were tested in the assay. Sera from normal volunteers indicate a background level of 1.68% in the assay (FIG. 10) whereas sera from 3 patients (patients 4, 7 and 19) indicate shed antigen levels significantly above background (FIG. 11). The signal from these sera decrease in a parallel manner with the gp75 standard as a function of increasing dilution (FIG. 12). Another panel of 88 breast cancer sera was tested in the assay and 13 sera are detected as positive with levels significantly above background, varying from 9.9-1511 ng/ml gp75 equivalents. There seems to be no correlation between the amount of shed antigen as measured by the sandwich gp75 IRMA and a commercially available diagnostic assay from Centocor (Table 6). The Centocor as say is an FDA-approved assay for the diagnosis of human breast cancer which has been commercially available for several years. The Centocor assay measures a mucin, and was positive for each of the 13 breast cancer sera that tested positive in the IRMA gp75 assay. The IRMA gp75 assay, however, shows a slightly different gp75 profile for each patient whereas the Centocor assay's measure of the mucin level is more standard for each patient. The differences in gp75 levels may be indicative of varying disease status for different patients.

CONCLUSION

It is understood that the hybrid micro-organisms, recombinant DNA molecules and proteins/polypeptides and methods applicable to them of this invention are not limited to those described in the preferred embodiments above. The hybrid organisms, recombinant DNA molecules and protein/polypeptides may be modified during production or subsequently by known methods to good advantage. For example, more efficient control sequences may be used for transcription of the c-erbB-2 sequences, mutations to reduce the synthesis of undesired products may be introduced, the protease levels in the host cells may be reduced, thermoinducible lysogens containing the c-erbB-2 sequences may be integrated into the host chromosome or other modifications and procedures may be carried out to increase the number of sequence copies in the cell or to increase the cell's productivity in producing the desired protein/polypeptide.

Various modifications of the invention in addition to those shown and described herein will become apparent to those

TABLE 6

Quantitation of Shed Antigen in Human Breast Cancer Sera in the
TAb 259/256 Sandwich IRMA, Comparison with the Centocor Assay

| Breast Cancer Serum Sample | IRMA gp75 equivalents (ng/ml)* | Centocor CA15-3 RIA (units/ml)** |
|---|---|---|
| 1 | 43.7 | 164 |
| 2 | 38.4 | >200 |
| 3 | 75.1 | <25 |
| 4 | 39.1 | 43 |
| 5 | 60.1 | >200 |
| 6 | 37.6 | >200 |
| 7 | 81.9 | 37 |
| 8 | 1511.0 | >200 |
| 9 | 9.9 | 98 |
| 10 | 27.8 | 43 |
| 11 | 10.0 | <200 |
| 12 | 104.6 | 139 |
| 13 | 19.8 | 75 |

*Less than 5.10 ng/ml is negative.
**Normals considered 13.9 ± 8 units.

The invention claimed is:

1. An assay to detect and quantitate antibodies in a mammalian body fluid that are specific for a glycoprotein that constitutes the c-erbB-2 external domain comprising the steps of:
   a) contacting a mammalian body fluid with a labeled c-erbB-2 external domain protein or polypeptide; and
   b) determining whether antibodies in said mammalian body fluid bind to said labeled c-erbB-2 external domain protein or polypeptide and the extent of said binding, wherein said binding indicates the presence of said antibodies, and the extent of binding indicates the quantity of said antibodies.

2. A method of screening for the presence of a c-erbB-2 associated malignancy in a mammal, comprising the steps of:
   (a) contacting a sample of body fluid from said mammal, suspected of containing antibodies that are c-erbB-2 external domain-specific, with a c-erbB-2 external domain protein or polypeptide;
   (b) incubating the body fluid sample under conditions and for a time sufficient to allow immunocomplexes to form; and
   (c) detecting the presence or absence of immunocomplexes formed between the c-erbB-2 external domain protein or polypeptide and antibodies in the body fluid sample specific for the c-erbB-2 external domain, thereby determining the presence or absence of the malignancy.

3. The method of claim 2 wherein the c-erbB-2-associated malignancy is selected from the group consisting of breast, ovarian, colon, stomach, liver, thyroid, brain, pancreatic, urinary tract, salivary gland and prostate cancer.

4. The method of claim 2 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

5. The assay according to claim 1 wherein said antibodies are specific for a fragment of said glycoprotein that constitutes the c-erbB-2 external domain.

6. The method of claim 4 wherein the reporter group is selected from the group consisting of radioisotopes, fluorophores, enzymes, luminescers and dye particles.

7. The method of claim 2 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

8. The method of claim 7 wherein the molecule capable of binding to the immunocomplexes is protein A.

9. The method of claim 7 wherein the reporter group is selected from the group consisting of radioisotopes, fluorophores, enzymes, luminescers, and dye particles.

10. The method of claim 2 wherein a reporter group is bound to the c-erbB-2 external domain protein or polypeptide, and wherein the step of detecting comprises removing substantially any unbound c-erbB-2 external domain protein or polypeptide and thereafter detecting the presence or absence of the reporter group.

11. The method of claim 10 wherein the reporter group is selected from the group consisting of radioisotopes, fluorophores, enzymes, luminescers, and dye particles.

12. A method for detecting changes in the level of antibodies that are c-erbB-2 external domain-specific in a human having or suspected of having a c-erbB-2 associated malignancy, comprising the steps of:
   (a) contacting a first body fluid sample from said human with a c-erbB-2 external domain protein or polypeptide;
   (b) incubating the sample under conditions and for a time sufficient to allow immunocomplexes to form;
   (c) detecting immunocomplexes formed between the c-erbB-2 external domain protein or polypeptide and antibodies in the sample that are specific for the c-erbB-2 external domain;
   (d) repeating steps (a), (b) and (c) on a second body fluid sample taken from the same human at a time subsequent to the first sample; and
   (e) comparing the number of immunocomplexes detected in the first and second body fluid samples, thereby determining whether a change in the level of antibody specific for the c-erbB-2 external domain has occurred.

13. The method of claim 12 wherein the c-erbB-2-associated malignancy is selected from the group consisting of breast, ovarian, colon, stomach, liver, thyroid, brain, pancreatic, urinary tract, salivary gland and prostate cancer.

14. The method of claim 12 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

15. The assay according to claim 1 wherein said mammalian body fluid is a human body fluid.

16. The method of claim 14 wherein the reporter group is selected from the group consisting of radioisotopes, fluorophores, enzymes, luminescers, and dye particles.

17. The method of claim 12 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

18. The method of claim 17 wherein the molecule capable of binding to the immunocomplexes is protein A.

19. The method of claim 17 wherein the reporter group is selected from the group consisting of radioisotopes, fluorophores, enzymes, luminescers, and dye particles.

20. The method of claim 12 wherein a reporter group is bound to the c-erbB-2 external domain protein or polypeptide, and wherein the step of detecting comprises removing substantially any unbound c-erbB-2 external domain protein or polypeptide and thereafter detecting the presence or absence of the reporter group.

21. The method of claim 20 wherein the reporter group is selected from the group consisting of radioisotopes, fluorophores, enzymes, luminescers, and dye particles.

22. A method of screening for neoplastic disease, diagnosing neoplastic disease, monitoring the disease status of a patient with neoplastic disease, or prognosticating the course of neoplastic disease in a patient and deciding upon a treatment protocol for a patient, comprising detecting and quantitating the levels of antibodies that are specific for the c-erbB-2 external domain in the patient's body fluid samples.

23. The method according to claim 22 performed after an operation to remove a tumor wherein the presence of said antibodies in a patient's body fluid sample is indicative of metastases.

24. An assay to detect and quantitate antibodies that are specific for the c-erbB-2 external domain in a mammalian body fluid comprising the steps of:
   a) contacting said mammalian body fluid with a labeled c-erbB-2 external domain protein or polypeptide, wherein said protein or polypeptide has been recombinantly produced; and
   b) determining whether antibodies in said mammalian body fluid bind to said labeled c-erbB-2 external domain protein or polypeptide and the extent of said binding, wherein said binding indicates the presence of said antibodies, and the extent of binding indicates the quantity of said antibodies.

25. A method of screening for the presence of a c-erbB-2 associated malignancy in a mammal, comprising the steps of:
   (a) contacting a sample of body fluid from said mammal, suspected of containing antibodies that are c-erbB-2 external domain-specific, with a recombinantly produced c-erbB-2 external domain protein or polypeptide;
   (b) incubating the body fluid sample under conditions and for a time sufficient to allow immunocomplexes to form; and
   (c) detecting the presence or absence of immunocomplexes formed between the recombinantly produced c-erbB-2 external domain protein or polypeptide and antibodies in the body fluid sample specific for the c-erbB-2 external domain, thereby determining the presence or absence of the malignancy.

26. The method of claim 25 wherein the c-erbB-2-associated malignancy is selected from the group consisting of breast, ovarian, colon, stomach, liver, thyroid, brain, pancreatic, urinary tract, salivary gland, and prostate cancer.

27. The method of claim 25 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

28. The method of claim 27 wherein the reporter group is selected from the group consisting of radioisotopes, fluorophores, enzymes, luminescers and dye particles.

29. The method of claim 25 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

30. The method of claim 29 wherein the molecule capable of binding to the immunocomplexes is protein A.

31. The method of claim 29 wherein the reporter group is selected from the group consisting of radioisotopes, fluorophores, enzymes, luminescers, and dye particles.

32. The method of claim 25 wherein a reporter group is bound to the recombinantly produced c-erbB-2 external domain protein or polypeptide, and wherein the step of detecting comprises removing substantially any unbound recombinantly produced c-erbB-2 external domain protein or polypeptide and thereafter detecting the presence or absence of the reporter group.

33. The method of claim 32 wherein the reporter group is selected from the group consisting of radioisotopes, fluorophores, enzymes, luminescers, and dye particles.

34. A method for detecting changes in the level of antibodies that are c-erbB-2 external domain-specific in a human having or suspected of having a c-erbB-2 associated malignancy, comprising the steps of:
   (a) contacting a first body fluid sample from said human with a recombinantly produced c-erbB-2 external domain protein or polypeptide;
   (b) incubating the sample under conditions and for a time sufficient to allow immunocomplexes to form;
   (c) detecting immunocomplexes formed between the recombinantly produced c-erbB-2 external domain protein or polypeptide and antibodies in the sample that are specific for the c-erbB-2 external domain;
   (d) repeating steps (a), (b) and (c) on a second body fluid sample taken from the same human at a time subsequent to the first sample; and
   (e) comparing the number of immunocomplexes detected in the first and second body fluid samples, thereby determining whether a change in the level of antibody specific for the c-erbB-2 external domain has occurred.

35. The method of claim 34 wherein the c-erbB-2 associated malignancy is selected from the group consisting of breast, ovarian, colon, stomach, liver, thyroid, brain, pancreatic, urinary tract, salivary gland and prostate cancer.

36. The method of claim 34 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

37. The method of claim 36 wherein the reporter group is selected from the group consisting of radioisotopes, fluorophores, enzymes, luminescers, and dye particles.

38. The method of claim 34 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

39. The method of claim 38 wherein the molecule capable of binding to the immunocomplexes is protein A.

40. The method of claim 38 wherein the reporter group is selected from the group consisting of radioisotopes, fluorophores, enzymes, luminescers, and dye particles.

41. The method of claim 34 wherein a reporter group is bound to the recombinantly produced c-erbB-2 external domain protein or polypeptide, and wherein the step of detecting comprises removing substantially any unbound recombinantly produced c-erbB-2 external domain protein or polypeptide and thereafter detecting the presence or absence of the reporter group.

42. The method of claim 41 wherein the reporter group is selected from the group consisting of radioisotopes, fluorophores, enzymes, luminescers, and dye particles.

43. A method of screening for neoplastic disease, diagnosing neoplastic disease, monitoring the disease status of a patient with neoplastic disease, or prognosticating the course of neoplastic disease in a patient and deciding upon a treatment protocol for a patient, comprising detecting and quantitating the levels of antibodies that are specific for the c-erbB-2 external domain in the patient's body fluid samples, wherein a recombinantly produced c-erbB-2 external domain protein or polypeptide is used.

44. The method according to claim 43 performed after an operation to remove a tumor wherein the presence of said antibodies in a patient's body fluid sample is indicative of metastases.

45. An assay to detect and quantitate antibodies that are specific for the c-erbB-2 external domain in a mammalian body fluid comprising the steps of:
   a) contacting said mammalian body fluid with a labeled anti-idiotype antibody to an antibody specific to a c-erbB-2 external domain protein or polypeptide; and
   b) determining whether antibodies in said mammalian body fluid bind to said labeled anti-idiotype antibody and the extent of said binding, wherein said binding indicates the presence of said antibodies, and the extent of binding indicates the quantity of said antibodies.

46. A method of screening for the presence of a c-erbB-2 associated malignancy in a mammal, comprising the steps of:
   (a) contacting a sample of body fluid from said mammal, suspected of containing antibodies that are c-erbB-2 external domain-specific, with an anti-idiotype antibody to an antibody specific to a c-erbB-2 external domain protein or polypeptide;
   (b) incubating the body fluid sample under conditions and for a time sufficient to allow immunocomplexes to form; and
   (c) detecting the presence or absence of immunocomplexes formed between the anti-idiotype antibody and antibodies in the body fluid sample specific for the c-erbB-2 external domain, thereby determining the presence or absence of the malignancy.

47. The method of claim 46 wherein the c-erbB-2-associated malignancy is selected from the group consisting of breast, ovarian, colon, stomach, liver, thyroid, brain, pancreatic, urinary tract, salivary gland, and prostate cancer.

48. The method of claim 46 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

49. The method of claim 48 wherein the reporter group is selected from the group consisting of radioisotopes, fluorophores, enzymes, luminescers and dye particles.

50. The method of claim 46 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

51. The method of claim 50 wherein the molecule capable of binding to the immunocomplexes is protein A.

52. The method of claim 50 wherein the reporter group is selected from the group consisting of radioisotopes, fluorophores, enzymes, luminescers, and dye particles.

53. The method of claim 46 wherein a reporter group is bound to the anti-idiotype antibody, and wherein the step of detecting comprises removing substantially any unbound anti-idiotype antibody and thereafter detecting the presence or absence of the reporter group.

54. The method of claim 53 wherein the reporter group is selected from the group consisting of radioisotopes, fluorophores, enzymes, luminescers, and dye particles.

55. A method for detecting changes in the level of antibodies that are c-erbB-2 external domain-specific protein in a human having or suspected of having a c-erbB-2 associated malignancy, comprising the steps of:
   (a) contacting a first body fluid sample from said human with an anti-idiotype antibody to an antibody specific to a c-erbB-2 external domain protein or polypeptide;
   (b) incubating the sample under conditions and for a time sufficient to allow immunocomplexes to form;
   (c) detecting immunocomplexes formed between the anti-idiotype antibody and antibodies in the sample that are specific to the c-erbB-2 external domain;
   (d) repeating steps (a), (b) and (c) on a second body fluid sample taken from the same human at a time subsequent to the first sample; and
   (e) comparing the number of immunocomplexes detected in the first and second body fluid samples, thereby determining whether a change in the level of antibody specific for the c-erbB-2 external domain has occurred.

56. The method of claim 55 wherein the c-erbB-2 associated malignancy is selected from the group consisting of breast, ovarian, colon, stomach, liver, thyroid, brain, pancreatic, urinary tract, salivary gland, and prostate cancer.

57. The method of claim 55 wherein a reporter group is bound to a second antibody capable of binding to the antibodies, and wherein the step of detecting comprises (a) removing substantially any unbound antibody, (b) adding the second antibody, (c) removing substantially any unbound second antibody, and (d) detecting the presence or absence of the reporter group.

58. The method of claim 57 wherein the reporter group is selected from the group consisting of radioisotopes, fluorophores, enzymes, luminescers, and dye particles.

59. The method of claim 55 wherein a reporter group is bound to a molecule capable of binding to the immunocomplexes, and wherein the step of detecting comprises (a) adding the molecule, (b) removing substantially any unbound molecule, and (c) detecting the presence or absence of the reporter group.

60. The method of claim 59 wherein the molecule capable of binding to the immunocomplexes is protein A.

61. The method of claim 59 wherein the reporter group is selected from the group consisting of radioisotopes, fluorophores, enzymes, luminescers, and dye particles.

62. The method of claim 55 wherein a reporter group is bound to the anti-idiotype antibody, and wherein the step of detecting comprises removing substantially any unbound anti-idiotype antibody and thereafter detecting the presence or absence of the reporter group.

63. The method of claim 62 wherein the reporter group is selected from the group consisting of radioisotopes, fluorophores, enzymes, luminescers, and dye particles.

64. A method of screening for neoplastic disease, diagnosing neoplastic disease, monitoring the disease status of a patient with neoplastic disease, or prognosticating the course of neoplastic disease in a patient and deciding upon a treatment protocol for a patient, comprising detecting and quantitating the levels of antibodies that are c-erbB-2 external domain-specific in the patient's body fluid samples, wherein an anti-idiotype antibody to an antibody specific for the c-erbB-2 external domain is used.

65. The method according to claim 64 performed after an operation to remove a tumor wherein the presence of said antibodies in a patient's body fluid sample is indicative of metastases.

66. The method according to claim 22, additionally comprising classifying a patient as to his or her chance of long term survival or to a time to relapse of the disease.

67. A method according to claim 22 wherein the neoplastic disease is a tumor of an organ having a secretory function.

68. A method according to claim 22 wherein the neoplastic disease is a tumor of epithelial origin.

69. The method according to claim 43, additionally comprising classifying a patient as to his or her chance of long term survival or to a time to relapse of the disease.

70. A method according to claim 43 wherein the neoplastic disease is a tumor of an organ having a secretory function.

71. A method according to claim 43 wherein the neoplastic disease is a tumor of epithelial origin.

72. The method according to claim 64, additionally comprising classifying a patient as to his or her chance of long term survival or to a time to relapse of the disease.

73. A method according to claim 64 wherein the neoplastic disease is a tumor of an organ having a secretory function.

74. A method according to claim 64 wherein the neoplastic disease is a tumor of epithelial origin.

* * * * *